(12) United States Patent
Waugh et al.

(10) Patent No.: US 9,918,848 B2
(45) Date of Patent: Mar. 20, 2018

(54) SPINAL IMPLANT SYSTEM AND METHOD

(71) Applicant: Warsaw Orthopedic, Inc., Warsaw, IN (US)

(72) Inventors: Lindsey G. Waugh, Memphis, TN (US); Anthony J. Melkent, Germantown, TN (US); Jonathan E. Blackwell, Arlington, TN (US); Thomas E. Drochner, Memphis, TN (US); Carrie L. Gowan, Memphis, TN (US); Bret Matthew Wilfong, Hernando, MS (US); Thomas A. Carls, Memphis, TN (US); Richard A. Hynes, Melbourne, FL (US); D. Hal Silcox, III, Atlanta, GA (US); John A. Cowan, Jr., Rome, GA (US); Jean-Pierre Mobasser, Indianapolis, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/494,381

(22) Filed: Sep. 23, 2014

(65) Prior Publication Data

US 2015/0100129 A1   Apr. 9, 2015

Related U.S. Application Data

(60) Provisional application No. 61/887,794, filed on Oct. 7, 2013.

(51) Int. Cl.
*A61F 2/44* (2006.01)
*A61B 17/70* (2006.01)
(Continued)

(52) U.S. Cl.
CPC .......... *A61F 2/442* (2013.01); *A61B 17/0206* (2013.01); *A61B 17/7059* (2013.01); *A61B 17/8042* (2013.01); *A61F 2/447* (2013.01); *A61F 2/4455* (2013.01); *A61F 2/4465* (2013.01); *A61F 2/4611* (2013.01); *A61F 2/4684* (2013.01); *A61B 2017/00004* (2013.01);
(Continued)

(58) Field of Classification Search
CPC .................................................. A61F 2/4611
USPC ........................................................ 623/17.16
See application file for complete search history.

(56) References Cited

U.S. PATENT DOCUMENTS

| 7,479,160 B2 * | 1/2009 | Branch | A61B 17/1671 623/17.11 |
| 8,268,000 B2 * | 9/2012 | Waugh | A61F 2/4465 623/17.16 |

(Continued)

FOREIGN PATENT DOCUMENTS

WO    2012103254 A2    8/2002

*Primary Examiner* — Ellen C Hammond
*Assistant Examiner* — Stuart S Bray

(57) ABSTRACT

A spinal implant comprises an implant body extending between an anterior surface and a posterior surface and includes a first vertebral engaging surface and a second vertebral engaging surface. The implant body includes an inner surface that defines at least one cavity that is oriented to implant a fastener oblique relative to a lateral axis of a subject body and adjacent an intervertebral space of the subject body. The implant body includes an oblique surface that defines at least one opening disposed in substantial alignment with the at least one cavity. Systems and methods are disclosed.

20 Claims, 20 Drawing Sheets

(51) Int. Cl.
*A61B 17/02* (2006.01)
*A61B 17/80* (2006.01)
*A61F 2/46* (2006.01)
*A61B 17/00* (2006.01)
*A61F 2/30* (2006.01)
*A61B 34/20* (2016.01)
*A61B 90/00* (2016.01)

(52) U.S. Cl.
CPC ............ *A61B 2034/2055* (2016.02); *A61B 2090/3966* (2016.02); *A61F 2002/3008* (2013.01); *A61F 2002/30092* (2013.01); *A61F 2002/30578* (2013.01); *A61F 2002/30787* (2013.01); *A61F 2002/30904* (2013.01); *A61F 2002/4475* (2013.01); *A61F 2220/0016* (2013.01); *A61F 2310/00017* (2013.01); *A61F 2310/00023* (2013.01); *A61F 2310/00029* (2013.01); *A61F 2310/00293* (2013.01); *A61F 2310/00359* (2013.01)

(56) References Cited

U.S. PATENT DOCUMENTS

| | | | | |
|---|---|---|---|---|
| 8,382,839 B1 * | 2/2013 | Wensel | A61B 17/864 | 623/17.11 |
| 8,641,765 B2 * | 2/2014 | Muhanna | A61F 2/447 | 623/17.11 |
| 8,740,983 B1 * | 6/2014 | Arnold | A61F 2/4455 | 623/17.16 |
| 8,840,668 B1 * | 9/2014 | Donahoe | A61B 17/1604 | 623/17.16 |
| 2003/0100950 A1 | 5/2003 | Moret | A61F 2/4465 | 623/17.16 |
| 2004/0102774 A1 * | 5/2004 | Trieu | A61B 17/7097 | 606/86 A |
| 2004/0133279 A1 * | 7/2004 | Krueger | A61B 17/7062 | 623/17.16 |
| 2005/0131536 A1 * | 6/2005 | Eisermann | A61F 2/447 | 623/17.11 |
| 2005/0216081 A1 * | 9/2005 | Taylor | A61F 2/44 | 623/17.11 |
| 2007/0255416 A1 * | 11/2007 | Melkent | A61F 2/4465 | 623/17.16 |
| 2008/0033562 A1 * | 2/2008 | Krishna | A61B 17/7011 | 623/17.16 |
| 2008/0091211 A1 * | 4/2008 | Gately | A61B 17/1671 | 606/99 |
| 2008/0183293 A1 * | 7/2008 | Parry | A61F 2/447 | 623/17.11 |
| 2008/0221694 A1 * | 9/2008 | Warnick | A61F 2/4465 | 623/17.16 |
| 2008/0294262 A1 * | 11/2008 | Levieux | A61F 2/447 | 623/17.16 |
| 2009/0105832 A1 * | 4/2009 | Allain | A61B 17/0642 | 623/17.16 |
| 2010/0070041 A1 * | 3/2010 | Peterman | A61F 2/447 | 623/17.16 |
| 2011/0040382 A1 * | 2/2011 | Muhanna | A61F 2/4455 | 623/17.11 |
| 2011/0112584 A1 * | 5/2011 | Frigg | A61B 17/80 | 606/289 |
| 2011/0160861 A1 * | 6/2011 | Jimenez | A61F 2/4465 | 623/17.16 |
| 2011/0166656 A1 * | 7/2011 | Thalgott | A61F 2/4455 | 623/17.16 |
| 2011/0166657 A1 * | 7/2011 | Thalgott | A61B 17/86 | 623/17.16 |
| 2011/0172776 A1 * | 7/2011 | Warnick | A61F 2/4465 | 623/17.16 |
| 2011/0178602 A1 * | 7/2011 | Ferree | A61B 17/1671 | 623/17.16 |
| 2011/0230971 A1 * | 9/2011 | Donner | A61B 17/70 | 623/17.16 |
| 2011/0295371 A1 * | 12/2011 | Moskowitz | A61B 17/0642 | 623/17.16 |
| 2011/0313528 A1 * | 12/2011 | Laubert | A61F 2/4455 | 623/17.16 |
| 2011/0319999 A1 * | 12/2011 | O'Neil | A61B 17/1659 | 623/17.16 |
| 2012/0010472 A1 | 1/2012 | Spann | | |
| 2012/0010714 A1 * | 1/2012 | Moskowitz | A61B 17/0642 | 623/17.16 |
| 2012/0010715 A1 * | 1/2012 | Spann | A61B 17/02 | 623/17.16 |
| 2012/0071978 A1 | 3/2012 | Suekamp et al. | | |
| 2012/0101580 A1 * | 4/2012 | Lechmann | A61B 17/86 | 623/17.16 |
| 2012/0136446 A1 * | 5/2012 | Krishna | A61B 17/7011 | 623/17.16 |
| 2012/0323327 A1 * | 12/2012 | McAfee | A61F 2/442 | 623/17.16 |
| 2013/0018466 A1 * | 1/2013 | Yu | A61F 2/4455 | 623/17.16 |
| 2013/0023994 A1 * | 1/2013 | Glerum | A61F 2/447 | 623/17.16 |
| 2013/0053894 A1 * | 2/2013 | Gamache | A61B 17/844 | 606/279 |
| 2013/0053964 A1 * | 2/2013 | Talwar | A61F 2/442 | 623/17.16 |
| 2013/0096683 A1 * | 4/2013 | Kube, II | A61F 2/442 | 623/17.16 |
| 2013/0110242 A1 * | 5/2013 | Kirwan | A61F 2/4455 | 623/17.16 |
| 2013/0123923 A1 * | 5/2013 | Pavlov | A61F 2/4455 | 623/17.16 |
| 2013/0150968 A1 * | 6/2013 | Dinville | A61F 2/447 | 623/17.16 |
| 2013/0158667 A1 * | 6/2013 | Tabor | A61F 2/4455 | 623/17.16 |
| 2013/0166027 A1 * | 6/2013 | Bellas | A61F 2/442 | 623/17.16 |
| 2013/0173004 A1 * | 7/2013 | Greenhalgh | A61F 2/4405 | 623/17.16 |
| 2013/0197643 A1 * | 8/2013 | Greenberg | A61F 2/442 | 623/17.16 |
| 2013/0218276 A1 * | 8/2013 | Fiechter | A61F 2/4455 | 623/17.16 |
| 2013/0231749 A1 * | 9/2013 | Armstrong | A61B 17/7059 | 623/17.16 |
| 2014/0039626 A1 * | 2/2014 | Mitchell | A61F 2/447 | 623/17.16 |
| 2014/0058515 A1 * | 2/2014 | Hawkins | A61F 2/4455 | 623/17.16 |
| 2014/0114415 A1 * | 4/2014 | Tyber | A61F 2/4455 | 623/17.16 |
| 2014/0172105 A1 * | 6/2014 | Frasier | A61F 2/4611 | 623/17.16 |
| 2014/0214166 A1 * | 7/2014 | Theofilos | A61F 2/4455 | 623/17.16 |
| 2014/0214167 A1 * | 7/2014 | Theofilos | A61F 2/4455 | 623/17.16 |
| 2014/0277478 A1 * | 9/2014 | Moore | A61F 2/442 | 623/17.16 |
| 2014/0277504 A1 * | 9/2014 | Forton | A61F 2/4611 | 623/17.16 |
| 2014/0309743 A1 * | 10/2014 | Falahee | A61F 2/4455 | 623/17.16 |
| 2015/0100126 A1 * | 4/2015 | Melkent | A61F 2/4455 | 623/17.16 |
| 2015/0173915 A1 * | 6/2015 | Laubert | A61F 2/447 | 623/17.16 |

* cited by examiner

SPINAL IMPLANT SYSTEM AND METHOD

CROSS-REFERENCE TO RELATED APPLICATION

This application claims the benefits of U.S. Provisional Patent Application No. 61/887,794 filed Oct. 7, 2013, the contents of which being hereby incorporated in its entirety by reference.

TECHNICAL FIELD

The present disclosure generally relates to medical devices for the treatment of musculoskeletal disorders, and more particularly to a spinal implant system and a method for treating a spine, which employ an oblique pathway.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy, corpectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. Certain spinal surgery approaches utilize a direct lateral approach to access lumbar disc spaces, however, these techniques present certain challenges due to the location of musculature and neural structures embedded therein.

This disclosure describes an improvement over these prior art technologies with the provision of specialized instrumentation, implants and techniques to allow for an oblique lateral surgical pathway to the lumbar disc spaces.

SUMMARY

Systems and methods of use for accessing disc spaces via an oblique lateral approach are provided. In some embodiments, a spinal implant comprises an implant body extending between an anterior surface and a posterior surface and includes a first vertebral engaging surface and a second vertebral engaging surface. The implant body includes an inner surface that defines at least one cavity that is oriented to implant a fastener oblique relative to a lateral axis of a subject body and adjacent an intervertebral space of the subject body disclosed. The implant body includes an oblique surface that defines at least one opening disposed in substantial alignment with the at least one cavity.

BRIEF DESCRIPTION OF THE DRAWINGS

The present disclosure will become more readily apparent from the specific description accompanied by the following drawings, in which.

DETAILED DESCRIPTION

Figure 1:
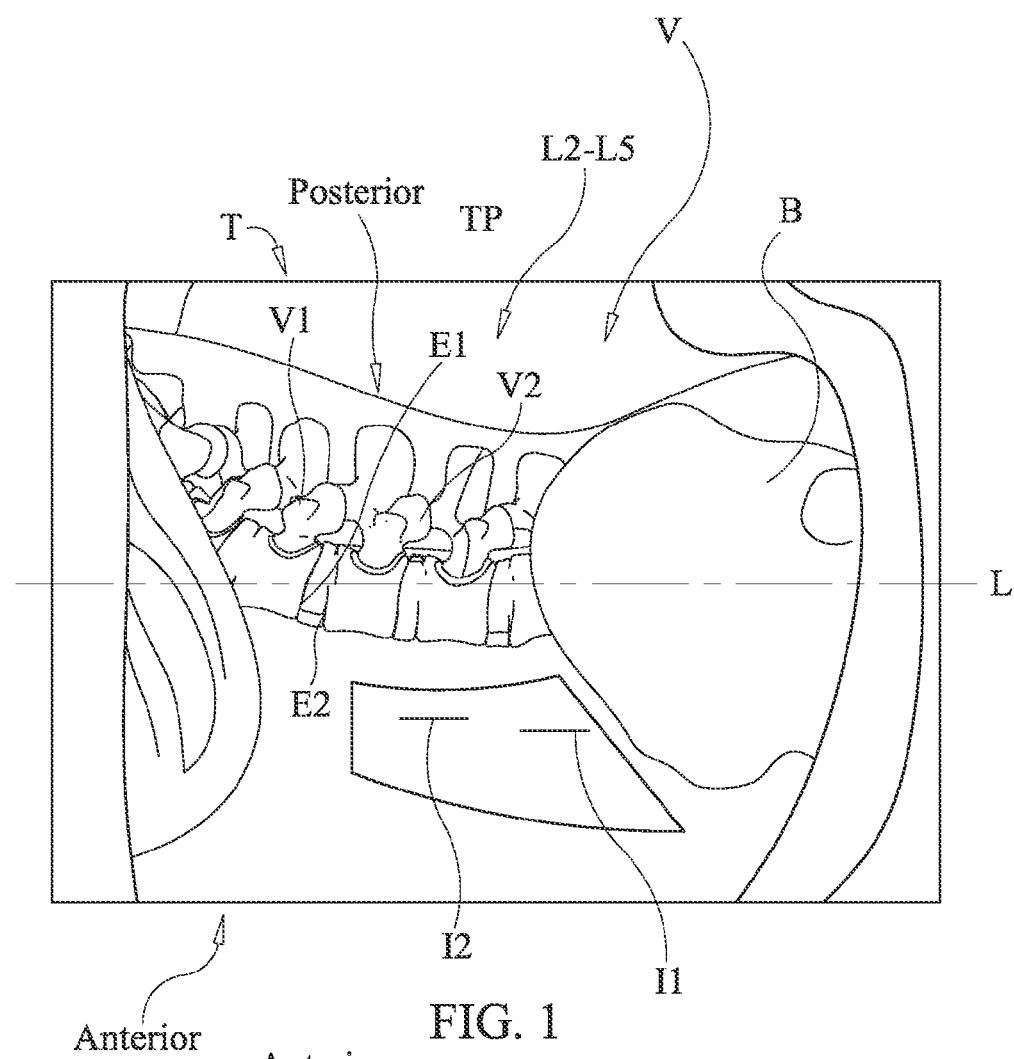
FIG. 1 is a plan view of a system for treating a body with a surgical procedure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine, which employ an oblique surgical pathway, which may include an oblique-lateral surgical pathway. In one embodiment, the systems and methods of the present disclosure are employed with a spinal joint and fusion, for example, with a cervical, thoracic, lumbar and/or sacral region of a spine.

In one embodiment, the surgical system is employed with a method including an oblique lateral interbody fusion (OLIF) procedure in the lower lumbar region between an L1 vertebral body and an L5 vertebral body using an antero-lateral operative corridor between a lateral psoas muscle and an anterior vasculature, such as, for example, the vena cava and aorta. In one embodiment, the patient is placed on their side, left side up, so as to position the vena cava on the right side of a centerline. In one embodiment, the surgical system avoids the psoas muscle thereby avoiding teasing apart the muscle fibers and disrupting nerves located in the psoas muscle in the L1-L5 vertebral region. In one embodiment, the psoas muscle is numbed and/or paralyzed the surgical procedure. In one embodiment, an anterior-most portion of the psoas muscle is pierced during the surgical procedure.

In one embodiment, the insertion pathway is disposed at an angle relative to a lateral axis of a patient body. In one embodiment, interbody implants and instruments are provided that facilitate positioning through the insertion pathway. In one embodiment, an interbody implant is disposed laterally in the disc space. In one embodiment, the interbody implant is positioned at an oblique angle relative to a lateral axis of the subject body. In one embodiment, the surgical pathway is oriented 0-45 degrees relative to a direct lateral axis of a subject body. In one embodiment, the surgical pathway is oriented 15-30 degrees relative to the direct lateral axis. In one embodiment, the surgical instruments are equipped with surgical navigation components, such as, for example, emitters mounted with the instruments and adjacent surgical device sensors employed with surgical navigation, microsurgical and image guided technologies may be employed to access, view and repair spinal deterioration or damage. In one embodiment, a trial is utilized to establish a starting point for insertion of an interbody implant.

In one embodiment, the surgical system includes an interbody implant having flanges that extend along the OLIF pathway for integrated fixation. In one embodiment, the surgical system includes an interbody implant with a plate. The interbody implant and plate can be inserted together or separately. In one embodiment, the surgical system includes an interbody implant having a zero profile with separate metal plates attached obliquely relative to a longitudinal axis of the interbody implant. In one embodiment, the surgical system includes an interbody implant having a zero profile with no plate but including obliquely-placed integrated fixation elements. In one embodiment, the surgical system includes an interbody implant including an angled edge curved towards an oblique surgical pathway.

In one embodiment, the surgical system includes an interbody implant having thread locking technology. In one embodiment, the surgical system includes an interbody implant having at least one flange that extends along the OLIF pathway for integrated fixation. In one embodiment, the surgical system includes an interbody implant provided with a plate. In one embodiment, the surgical system includes an interbody implant having radiopaque markers to facilitate positioning of the interbody implant.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-8, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TOP), HA-TOP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 2:
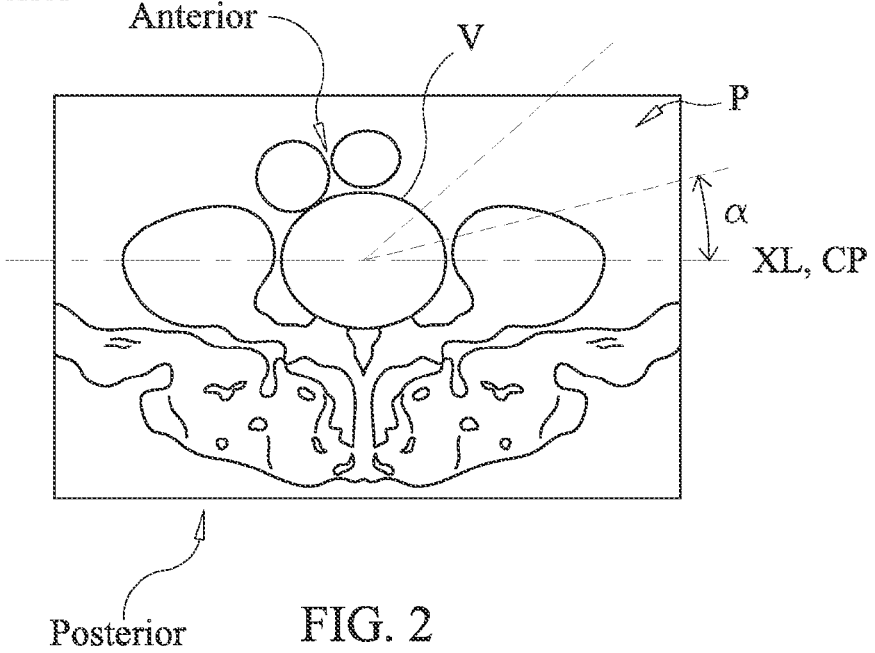
FIG. 2 is a plan view of a system for treating a body with a surgical procedure.

Spinal implant system 10 is employed, for example, with a fully open surgical procedure, a minimally invasive procedure, including percutaneous techniques, and mini-open surgical techniques to deliver and introduce instrumentation and/or an implant, such as, for example, an interbody implant, at a surgical site within a subject body B of a patient, which includes, for example, a spine having vertebrae V, as shown in FIGS. 1 and 2. In some embodiments, the implant can include spinal constructs, such as, for example, bone fasteners, spinal rods, connectors and/or plates.

Figure 8:
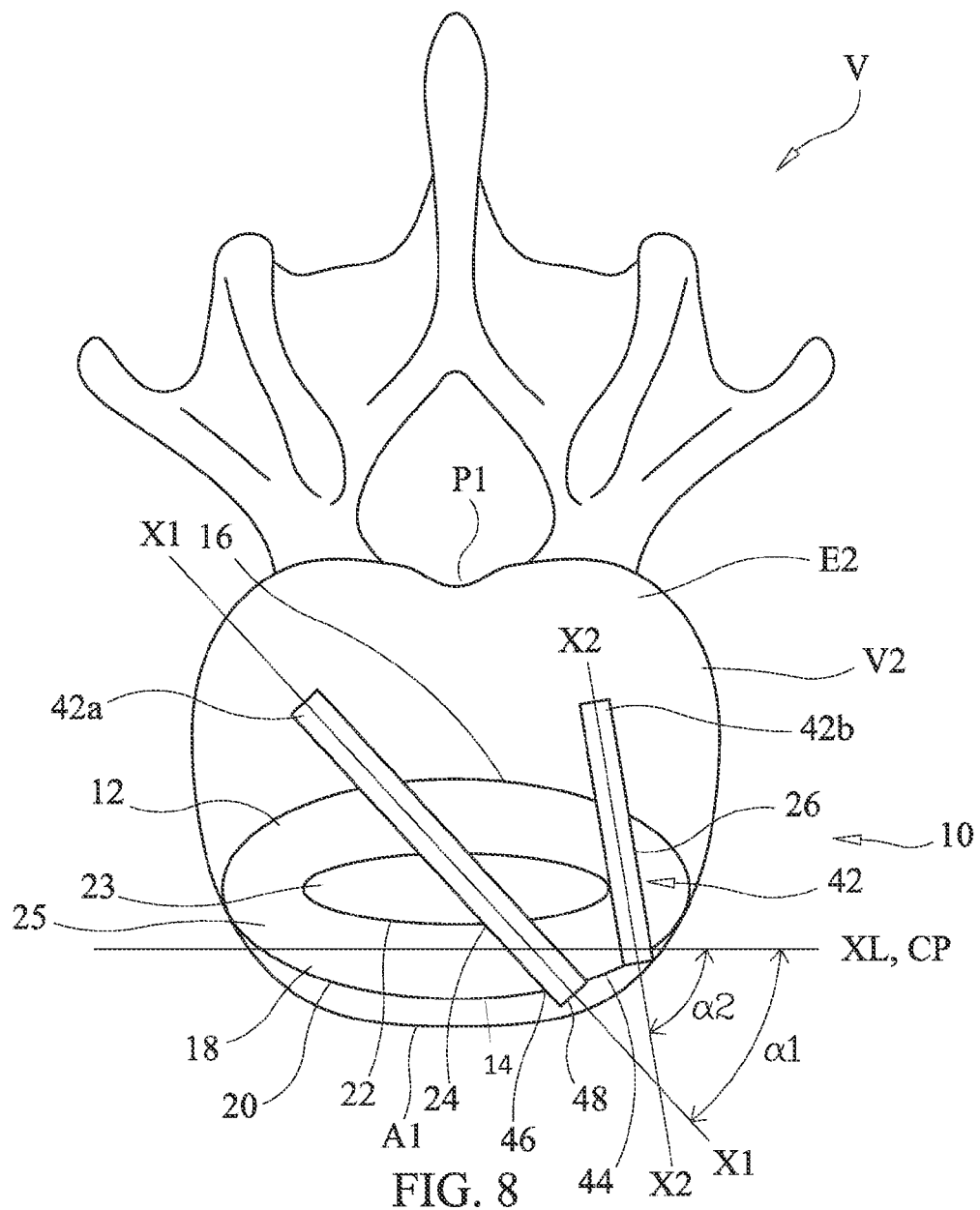
FIG. 8 is a plan view of components of one embodiment of a system in accordance with the principles of the present disclosure disposed with vertebrae.

Spinal implant system 10 includes an implant body, such as, for example, an interbody cage 12, as shown in FIG. 8. Cage 12 extends between an anterior surface 14 and a posterior surface 16. Anterior surface 14 is configured to face an anterior side of body B and be disposed adjacent an anterior portion of vertebrae, such as, for example an anterior portion A1 of one or more intervertebral spaces of the L2-L5 vertebral levels of vertebrae V. Posterior surface 16 is configured to face a posterior side of body B and be disposed adjacent a posterior portion of vertebrae, such as, for example a posterior portion P1 of one or more intervertebral spaces of the L2-L5 vertebral levels of vertebrae V.

Cage 12 includes a first vertebral engaging surface 18 and a second vertebral engaging surface 20. Surface 18 may be substantially planar and/or formed with a convex or angled surface and configured to engage endplate tissue of a vertebral body, such as, for example, an endplate E1 of a V1 vertebral level, as shown in FIG. 1. Surface 20 is configured to engage endplate tissue of a vertebral body, such as, for example, an endplate E2 of a V2 vertebral level, as shown in FIGS. 1 and 8. In some embodiments, surfaces 18, 20 may be rough, textured, porous, semi-porous, dimpled, knurled, toothed, grooved and/or polished such that it facilitates engagement with tissue. In some embodiments, the vertebral tissue may include intervertebral tissue, endplate surfaces and/or cortical bone. In some embodiments, surfaces 18, 20 may both be formed with a convex shape to better conform to the anatomy of a vertebral endplate.

Cage 12 may have a substantially oval cross section configuration and includes an inner surface 22 that defines an opening 23 configured to receive an agent, which may include bone graft (not shown) and/or other materials, as described herein, for employment in a fixation or fusion treatment. In some embodiments, the cross-sectional geometry of cage 12 may have various configurations, such as, for example, round, cylindrical, oblong, triangular, rectangular, polygonal having planar or arcuate side portions, irregular, uniform, non-uniform, consistent, variable, horseshoe shape, U-shape or kidney bean shape.

Inner surface 22 defines cavities, such as, for example, a screw hole 24 and a screw hole 26, as shown in FIG. 8. In some embodiments, cavities 24, 26 may be internally threaded or substantially smooth and/or flat. Screw hole 24 extends along the body of cage 12 in a transverse configuration relative to the surfaces of cage 12, described herein, for fixation with tissue. Screw hole 24 is oriented with the body of cage 12 in substantial alignment with an oblique surgical pathway P formed in body B, as described herein. Surgical pathway P is oriented oblique relative to a lateral axis XL of body B. In some embodiments, surgical pathway P is disposed at an oblique angle α relative to axis XL. In some embodiments, angle α is in a range of approximately 0-45 degrees. In some embodiments, substantial alignment of all or only a portion of screw hole 24 with all or only a portion of surgical pathway P includes co-axial, spaced apart, offset, angularly offset and/or parallel alignment.

Screw hole 24 defines an axis X1 oriented oblique relative to axis XL such that screw hole 24 implants a fastener, as described herein, oblique relative to axis XL and adjacent portion A1 Axis XL lies in a coronal plane CP defined by body B in substantial alignment with one or more intervertebral spaces of the L2-L5 vertebral levels, as shown in FIG. 2. Axis XL (FIG. 2) also lies in a transverse plane TP, as shown in FIG. 1, defined by body B such that planes CP, TP intersect adjacent axis XL. Vertebrae V defines a substantially longitudinal axis L, which lies in a sagittal plane of body B.

Axis X1 is disposed in substantial alignment with surgical pathway P and at an oblique angle α1 relative to axis XL. In some embodiments, angle α1 is in a range of approximately 0-45 degrees. In one embodiment, angle α1 is oriented approximately 15-30 degrees relative to axis XL and substantially aligned with surgical pathway P such that screw hole 24 is configured to receive a fastener via surgical pathway P. In some embodiments, screw hole 24 is also disposed at an angular orientation relative to plane CP and/or axis XL such that a fastener is delivered to a surgical site including an intervertebral space of one or more of the L2-L5 vertebral levels via surgical pathway P and oriented to penetrate endplate tissue of a vertebral body, such as, for example, endplate E1. In some embodiments, screw hole 24 and/or the body of cage 12 may be disposed at an angular orientation relative to plane CP and/or axis XL such that a fastener is oriented to penetrate endplate tissue of a vertebral body.

Figure 11:
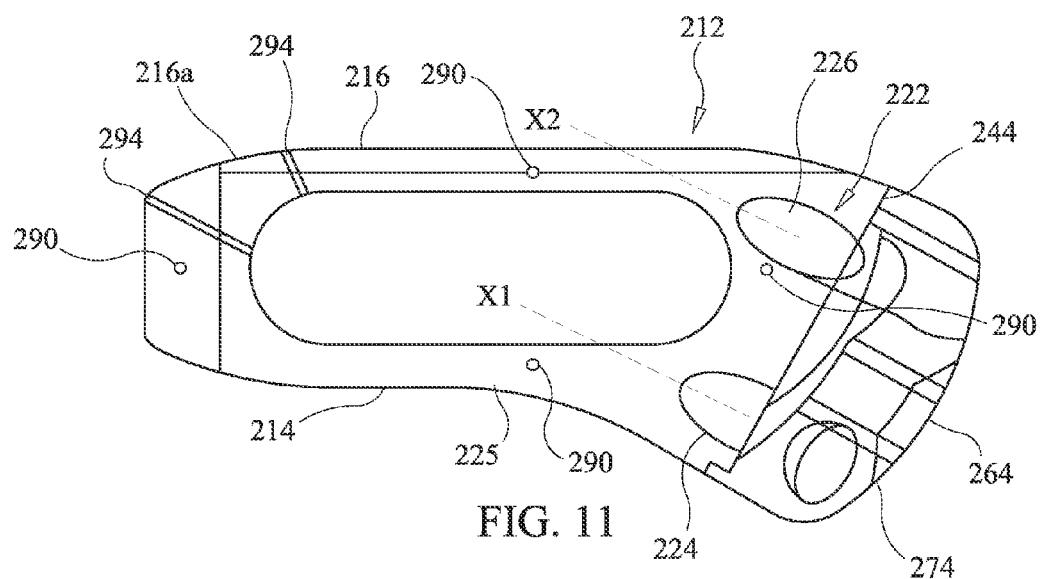
FIG. 11 is a side view of components of one embodiment of a system in accordance with the principles of the present disclosure.

Outer surface 25 includes an oblique surface 44 that defines an opening 46 disposed in communication and substantial alignment with screw hole 24. Oblique surface 44 is oriented with cage 12 and in substantial alignment with surgical pathway P. Opening 46 is configured to guide a fastener into screw hole 24 relative to axis XL and in substantial alignment with surgical pathway P. In some embodiments, oblique surface 44 is configured for mating engagement with a surgical instrument, such as, for example, an inserter, which delivers cage 12 adjacent a surgical site via surgical pathway P, as described herein. In some embodiments, oblique surface 44 comprises an oblique extension, such as, for example, as shown in FIG. 11, which shows an oblique surface, such as, for example, a flange 244, such that the proximal/anterior corner of cage 12 is asymmetric.

Screw hole 26 extends along the body of cage 12 in a transverse configuration relative to the surfaces of cage 12, described herein, for fixation with tissue. Screw hole 26 is oriented with the body of cage 12 in substantial alignment with surgical pathway P. In some embodiments, substantial alignment of all or only a portion of screw hole 26 with all or only a portion of surgical pathway P includes co-axial, spaced apart, offset, angularly offset and/or parallel alignment.

Figure 6:
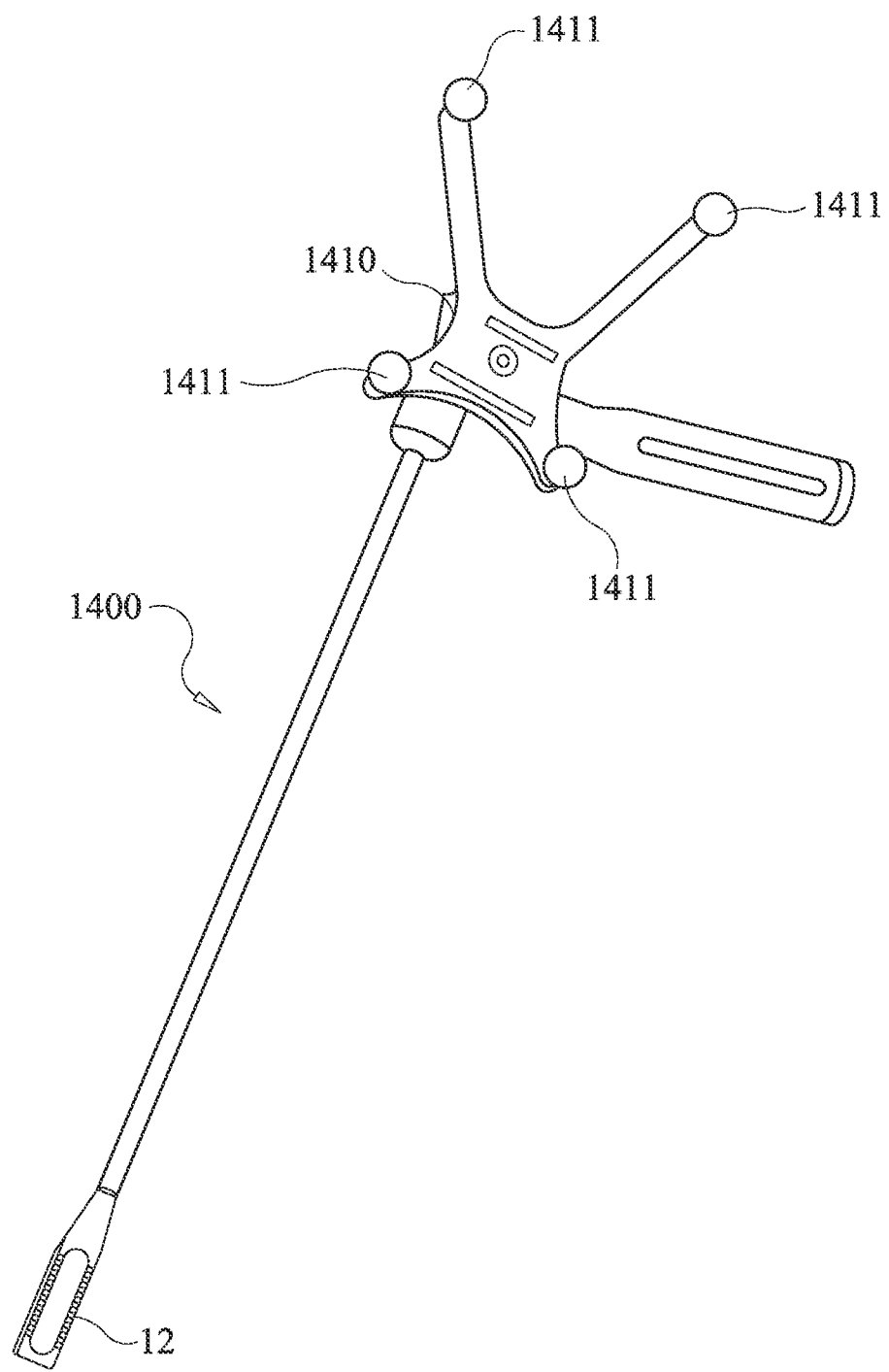
FIG. 6 is a perspective view of components of one embodiment of a system in accordance with the principles of the present disclosure.
Figure 7:
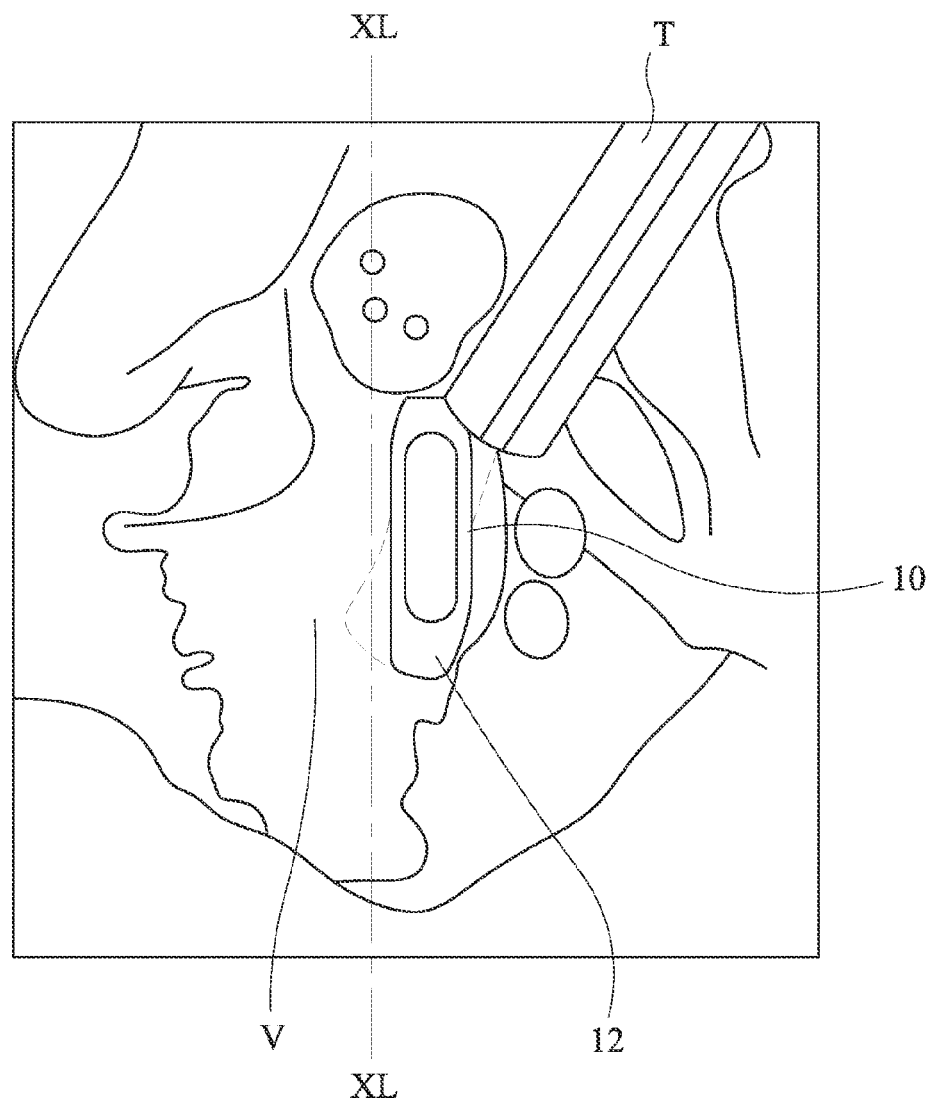
FIG. 7 is an axial view of components of the system and body shown in FIG. 4.

Screw hole 26 defines an axis X2 oriented oblique relative to axis XL such that screw hole 26 implants a fastener, as described herein, oblique relative to axis XL and adjacent portion A1. Axis X2 is disposed in substantial alignment with surgical pathway P and at an oblique angle α2 relative to axis XL. In some embodiments, angle α2 is in a range of approximately 0-45 degrees. In one embodiment, angle α2 is oriented approximately 15-30 degrees relative to axis XL and substantially aligned with surgical pathway P such that screw hole 26 is configured to receive a fastener via surgical pathway P. In some embodiments, screw hole 26 is also disposed at an angular orientation relative to plane CP and/or axis XL such that a fastener is delivered to a surgical site including an intervertebral space of one or more of the L2-L5 vertebral levels via surgical pathway P and oriented to penetrate endplate tissue of a vertebral body, such as, for example, endplate E2. In some embodiments, screw hole 26 and/or the body of cage 12 may be disposed at an angular orientation relative to plane CP and/or axis XL such that a fastener is oriented to penetrate endplate tissue of a vertebral body. In some embodiments, angle α, α1 and/or α2 may be equal, substantially equivalent and/or different. In some embodiments, surgical pathway P, axis X1 and/or axis X2 may be co-axial, spaced apart, offset, angularly offset and/or parallel alignment. In some embodiments, system 10 can include a screwdriver or inserter comprising navigation components, as shown in FIG. 6, to establish and maintain surgical pathway P and/or ensure that the screw placement is avoiding the anterior vasculature or psoas.

Oblique surface 44 defines an opening 48 disposed in communication and substantial alignment with screw hole 26. Opening 48 is configured to guide a fastener into screw hole 26 relative to axis XL and in substantial alignment with surgical pathway P. In some embodiments, the cross section configurations of screw holes 24, 26 may be, such as, for example, oval, oblong, triangular, square, polygonal, irregular, uniform, non-uniform, offset, staggered, undulating, arcuate, variable and/or tapered. In some embodiments, surface 22 may have alternate surface configurations to define cavities, similar to screw holes 24, 26, for receiving fasteners, such as, for example, nails, pins or blades, and/or include non-threaded portions.

Figure 14:
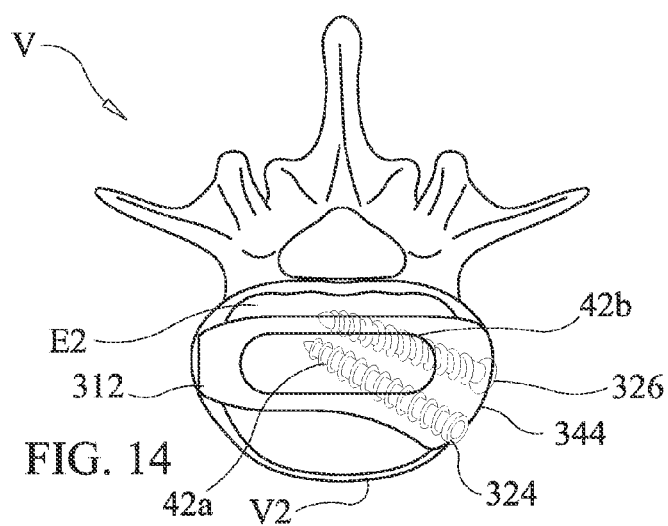
FIG. 14 is a plan view of components of FIG. 16 disposed with vertebrae with fasteners.

Spinal implant system 10 includes one or more fasteners 42, such as, for example, as shown in FIG. 14, for attaching cage 12 to bone, as described herein. In some embodiments, fasteners 42a and 42b may be engaged with tissue, such as, for example, the bony structures of a vertebral body in various orientations, such as, for example, series, parallel, offset, staggered and/or alternate vertebral levels. In some embodiments, one or more of fasteners 42 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Fastener 42 comprises a first portion, such as, for example, a head and a second portion, such as, for example, an elongated shaft configured for penetrating tissue. The head includes an engagement portion configured for engagement with a surgical instrument. The shaft has a cylindrical cross section configuration and includes an outer surface having an external thread form. In some embodiments, the external thread form may include a single thread turn or a plurality of discrete threads. In some embodiments, other engaging structures may be located on the shaft, such as, for example, nail configuration, barbs, expanding elements, raised elements and/or spikes to facilitate engagement of the shaft with tissue, such as, for example, vertebrae.

In some embodiments, all or only a portion of the shaft may have alternate cross section configurations, such as, for example, oval, oblong, triangular, square, polygonal, irregular, uniform, non-uniform, offset, staggered, undulating, arcuate, variable and/or tapered. In some embodiments, the outer surface of the shaft may include one or a plurality of openings. In some embodiments, all or only a portion of the outer surface of the shaft may have alternate surface configurations, such as, for example, smooth and/or surface configurations to enhance fixation with tissue, such as, for example, rough, arcuate, undulating, porous, semi-porous, dimpled, polished and/or textured. In some embodiments, all or only a portion of the shaft may be cannulated.

In some embodiments, system 10 may comprise various surgical instruments, such as, for example, drivers, extenders, reducers, spreaders, distractors, blades, clamps, forceps, elevators and drills, which may be alternately sized and dimensioned, and arranged as a kit. In some embodiments, system 10 may comprise the use of microsurgical and image guided technologies, such as, for example, surgical navigation components employing emitters and sensors, which may be employed to track introduction and/or delivery of the components of system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

In assembly, operation and use, as shown in FIGS. 1-8, spinal implant system 10, similar to the systems described herein, is employed with a surgical procedure for treatment of a spinal disorder, such as those described herein, affecting a section of a spine of a patient. System 10 may also be employed with other surgical procedures. To treat the affected section of vertebrae V of a subject body B of a patient, body B is disposed in a side orientation, as shown in FIG. 1, relative to a surgical fixed surface, such as, for example, surgical table T configured for supporting body B. Body B is placed on a side, left side up such that the vena cava, being oriented to the right of a centerline of body B, is positioned further away from pathway P. Body B is oriented such that the OLIF procedure can be performed obliquely in front of psoas muscle to provide direct access to one or more intervertebral spaces of the L2-L5 vertebral levels of vertebrae V while avoiding selected muscular and abdominal anatomical structures, such as, for example anterior vasculature. In some embodiments, placement of body B on its side facilitates access to surgical pathway P that is disposed at oblique angle α relative to axis XL. In some embodiments, placement of body B on its side facilitates natural movement of the abdominal contents away for pathway P via the effect of gravity. In some embodiments, placement of body B on its side allows the surgeon to access pathway P while standing in a natural and ergonomic posture. In some embodiments, needle electrodes may be placed in innervated muscles in the legs of body B to monitor affected nerve roots throughout the procedure.

In some embodiments, electrodes, such as, for example, electrodes used with neural integrity monitoring systems, may not be necessary as the pathway P may avoid nerve roots as well as the neural structures in the psoas muscle that are encountered along a lateral approach. In some embodiments, the psoas muscle is completely paralyzed during the surgical procedure as there is no need to monitor or located nerves present in the psoas muscle as the psoas muscle is avoided along the oblique pathway P. Paralyzing the psoas muscle facilitates manipulation and/or retraction of the psoas muscle during the surgical procedure.

As shown in FIG. 1, the L2 and L5 disc spaces, lower ribs and iliac crest can be marked on the skin as landmarks. In some embodiments, for example, a single vertebral level procedure, body B is marked 4-10 centimeters (cm) anterior to the midsection of the target disc (or approximately one third of the distance from the top of the iliac crest to the umbilicus). A 3 cm to 6 cm vertical, horizontal or oblique incision 11 is made in tissue of body B. In some embodiments, for example, a two vertebral level procedure, body B is marked 4-10 cm anterior to the midsection of the intervening vertebral body and an incision 12 is made in tissue of body B. In one embodiment, the lumbar lordosis of the operative levels can be marked on the skin to determine the angle in line with the disc space.

In some embodiments, the subcutaneous fat layers are dissected until the abdominal musculature is reached. In some embodiments, a mono-polar cautery can be utilized for hemostasis, and a small self-retaining retractor can be used for initial dissection of the skin and subcutaneous layer. In some embodiments, the external oblique fascia is the first plane encountered and is the only layer that will need to be sharply incised. In some embodiments, a clamp is used to bluntly spread through the fibers of the external oblique, internal oblique, and transversalis muscles. In some embodiments, dissection is performed in line with the muscle fibers as these muscle layers run in opposite directions.

In some embodiments, an index finger is utilized to follow the internal abdominal wall posteriorly down to the psoas muscle. In some embodiments, a finger or a blunt instrument is used to sweep the peritoneal contents, including the ureter, which reflects with the peritoneum, and the retroperitoneal fat anteriorly past the anterior portion of the psoas clearing to the anterior vertebral body.

In some embodiments, direct visualization may be employed in addition to tactile feel to ensure a safe approach to the disc space free from vascular, peritoneal and nerve obstructions. Fat overlying the psoas muscle is swept in a cephalad and caudal direction as well as dorso-ventral with handheld retractors. Use of hand-held retractors placed between peritoneal contents and the probe minimizes the risk of injury to ureters and vascular structures anteriorly. In some embodiments, a Kitner or cloth-based dissector may be used to sweep soft tissue structures anteriorly. In some embodiments, system 10 may include individual retractors, such as, for example, that shown in FIG. 3A, such that individual blades b1, b2, b3 may be inserted independently. In some embodiments, system 10 may include retractors such that no further probe is required. In some embodiments, system 10 may include retractors constrained via frame or semi-constrained using elastic or partial frame.

Figure 3:
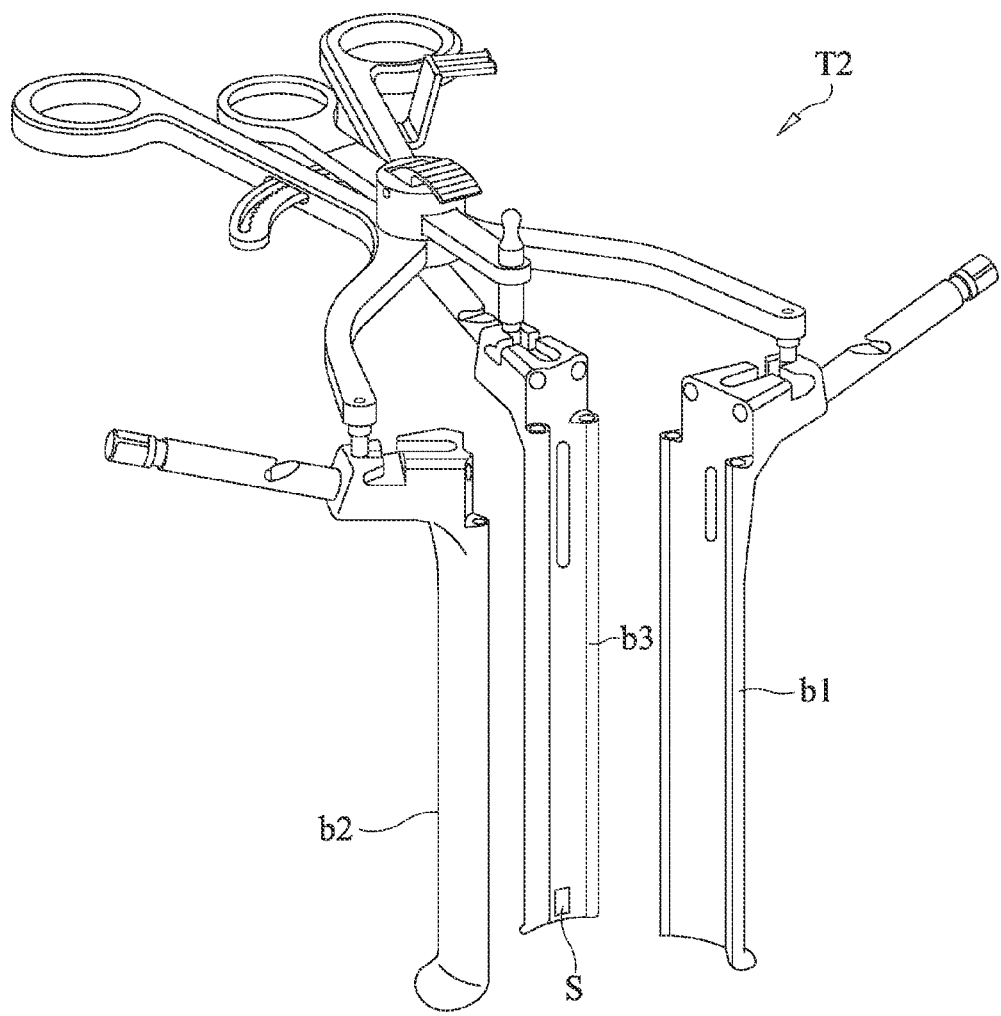
FIG. 3 is a perspective view of components of one embodiment of a system in accordance with the principles of the present disclosure.
Figure 3A:
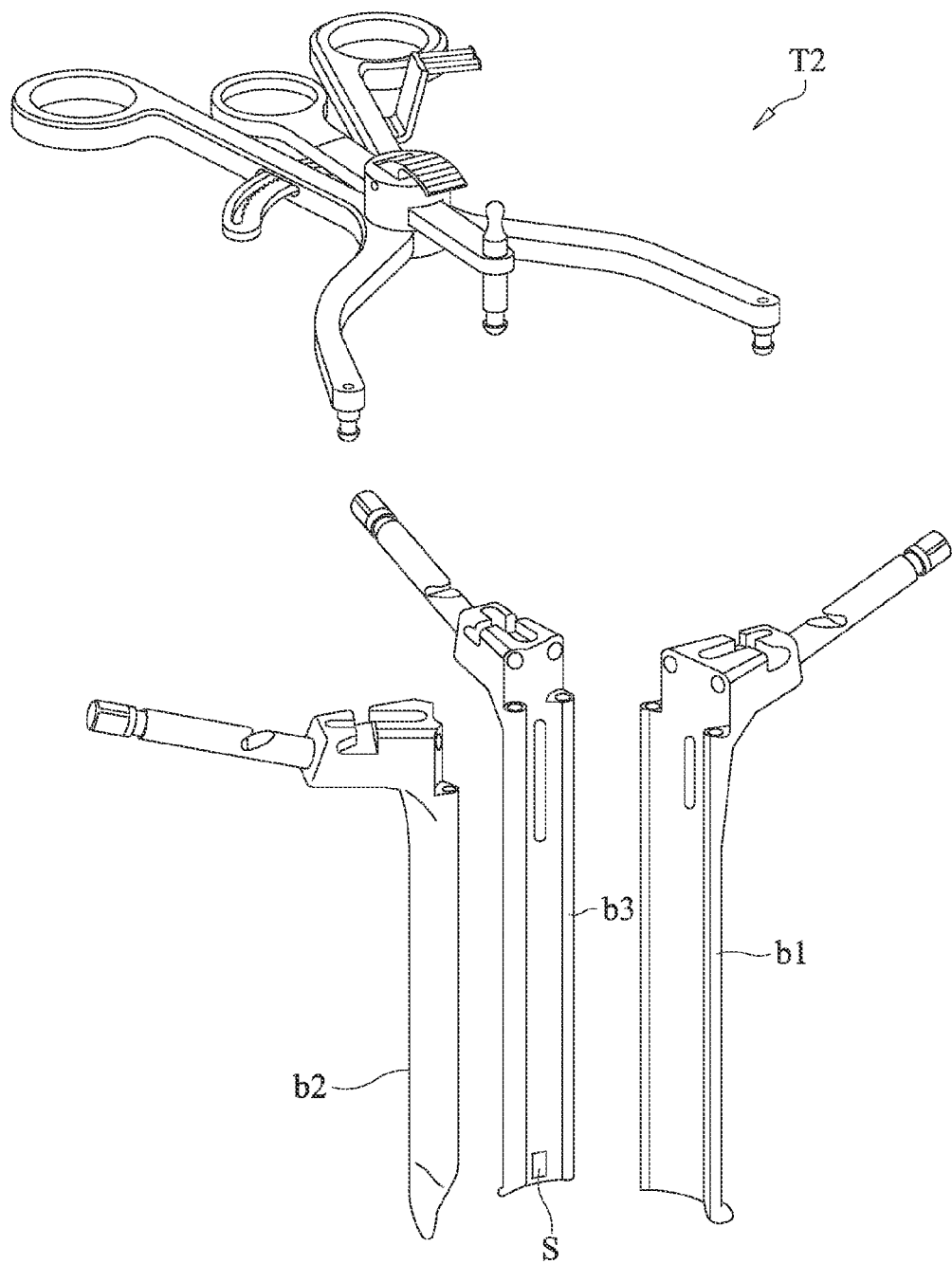
FIG. 3A is a perspective view of the components shown in FIG. 3 with parts separated.
Figure 4:
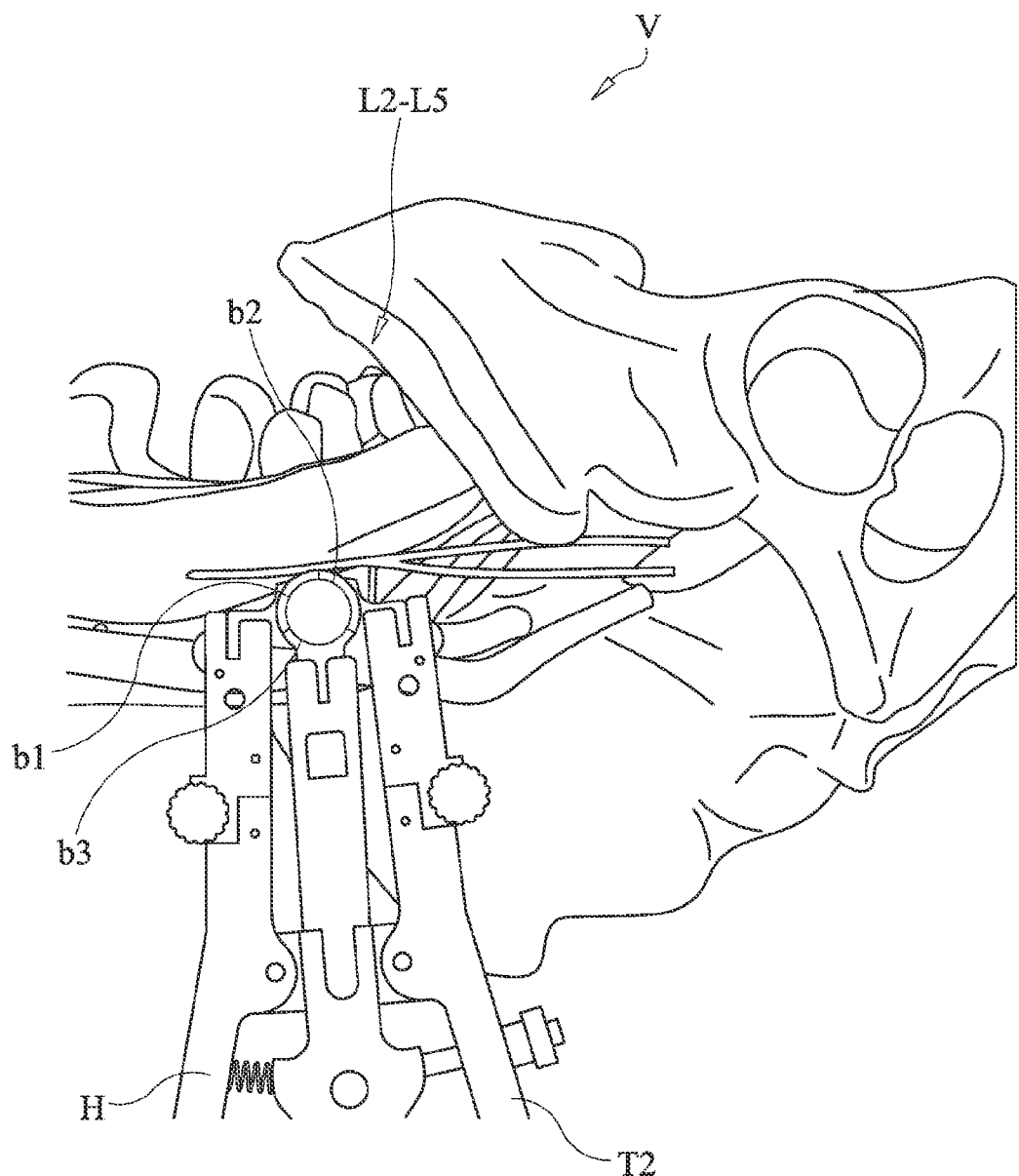
FIG. 4 is a perspective view of components of one embodiment of a system in accordance with the principles of the present disclosure disposed with a subject body.

In some embodiments, as shown in FIGS. 3, 3A and 4, a surgical instrument, such as, for example, a retractor T2 is disposed with incision I1 and/or I2 and in communication with surgical pathway P for spacing tissue. Retractor blades b1, b2, b3 may be inserted simultaneously as part of a unitary retractor instrument around one or more intervertebral spaces of the L2-L5 vertebral levels to protect vessels. In some embodiments, as shown in FIGS. 3 and 3A, a semi-constrained retractor system with separable blades may be used to sequentially and/or independently insert blades b1, b2, b3. An anterior blade b3 is oriented toward the anterior vasculature to secure protection of the aorta and vena cava. Posterior blades b1 and b2 are oriented toward the psoas to limit muscle creep and protect the muscle and neural elements. Blade b3 may have an elevation that permits direct visualization of a smooth pin placement. In some embodiments, the pin is blunt nosed to push away vascular structures and the threads are smooth to prevent wrapping up soft tissue. In some embodiments, a screw is malleted or screwed in and secures on one side of blade b1. In some embodiments, blade b3 may be equipped with a curved distal end to sweep and/or elevate vascular structures away from the surgical site. In one embodiment, anterior blade b3 may be provided with sensors S for detecting and/or measuring blood flow near the surgical site to ensure that the most relevant and sensitive vascular structures near the surgical site are safely separated from the oblique-lateral and/or oblique spinal surgical pathway. Sensors S may include, such as, for example, piezoelectric elements; ultrasound emitters and/or receivers, flowmeters; oximeters; pulse meters; and/or other available medical devices useful for identifying and/or localizing blood vessels. In some embodiments, anterior blade b3 may be clear, translucent, or a substantially clear material, such as, for example, a clear polymer, to allow a surgeon to directly visualize structures on the anterior side of anterior blade b3 during the surgical procedure. In some embodiments, blade b3 may also be longer in length than blades b1 and b2 and include a "spoon" shaped or curved end portion to better curve around the anterior side of a vertebral body, which may serve both to protect the vasculature and secure itself in place by more securely abutting the vertebral body.

Blade b3 is disposed with incision I1 and/or I2 and about one or more intervertebral spaces of the L2-L5 vertebral levels. In some embodiments, an annulotomy and/or discectomy is performed with a surgical instrument with x-ray confirmation of the starting point that is central on one or more intervertebral spaces of the L2-L5 vertebral levels. In some embodiments, system 10 includes a semi-constrained retractor that facilitates minimal tissue pressures on surrounding abdominal structures and provides flexibility such that its blades rotate on a fixed pin allowing greater degrees of freedom of movement and working angles for a practitioner.

A probe is preferably passed in front of, anterior to, or alternately through the anterior portion of the psoas and into the disc space to secure its location. In one embodiment, the oblique angle and lordotic angle of the probe as it enters the disc space is assessed preoperatively and measured intraoperative using image guidance or using a mechanical or digital protractor. Fluoroscopy, image guidance and/or surgical navigation, as described herein and shown in FIG. 6, with regard to the components of system 10, is used to confirm proper probe alignment into the disc space. In some embodiments, a guide wire is placed through a cannula into the disc space and positioning is confirmed with fluoroscopy. In some embodiments, with the guide wire and/or dilators and/or retractors in place and impacted into the annulus for firm fixation, sequential dilation is used to spread the fibers of the abdominal musculature to a diameter of 22 millimeters. Instruments, such as, for example, a Cobb, mallet, shaver, serrated curettes, rasp, a ring curette, a uterine curette and/or combo tools are utilized to perform a discectomy of the disc space. The instruments enter body B obliquely through the retractor and can be turned orthogonally to allow the surgeon to work orthogonally across the disc space. The disc space is distracted until adequate disc space height is obtained.

In some embodiments, an anterior longitudinal ligament (ALL) release procedure can be performed using an OLIF approach post-discectomy. For example, loosening the ALL can be performed by placing holes or partial cuts in the ALL such that the OLIF surgical pathway is immediately closer to the ALL.

Figure 5:
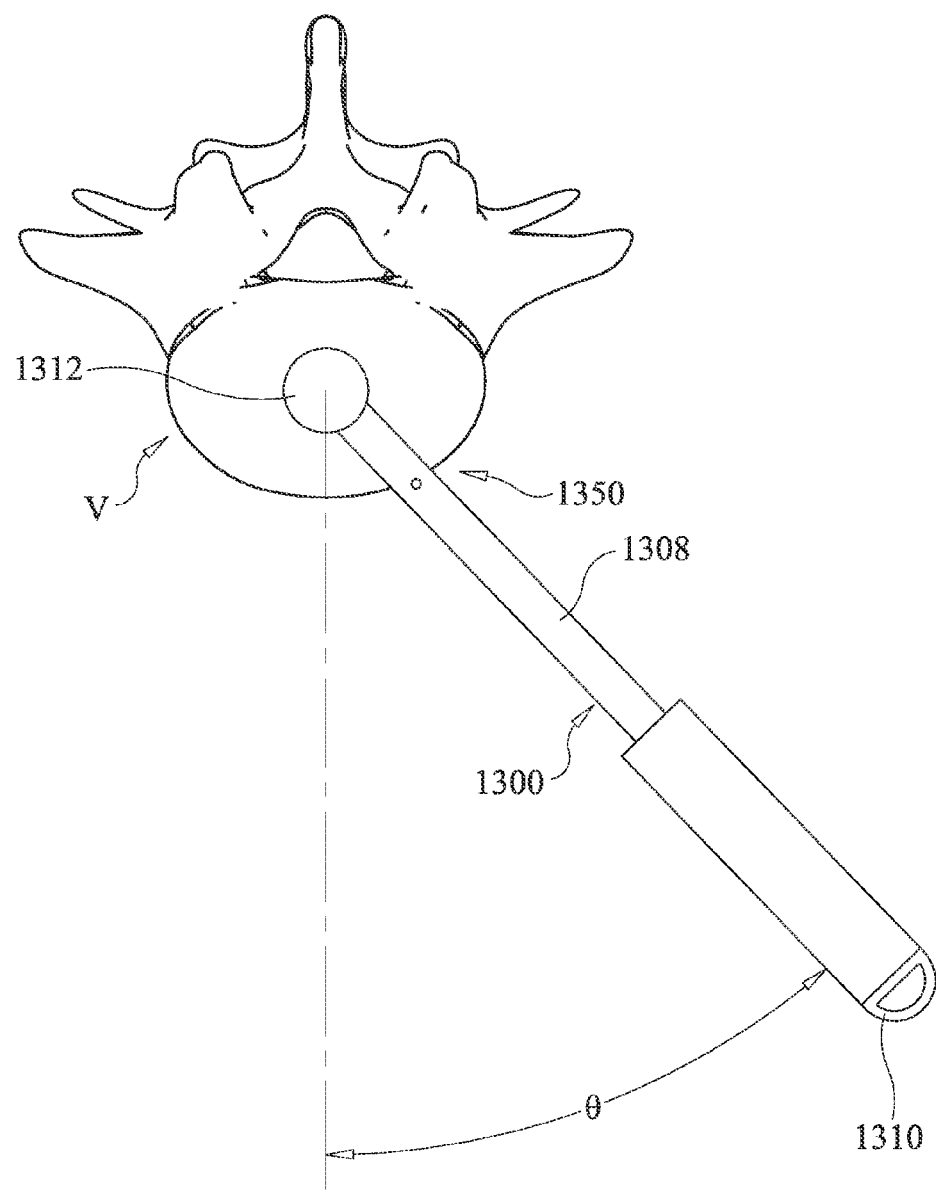
FIG. 5 is a perspective view of components of one embodiment of a system in accordance with the principles of the present disclosure.

In some embodiments, a discectomy is performed via surgical pathway. In some embodiments, trial implants are delivered along surgical pathway P and used to distract one or more intervertebral spaces of the L2-L5 vertebral levels and apply appropriate tension in the intervertebral space allowing for indirect decompression. In one embodiment, a direct decompression of the disc space is performed by removing a portion of a herniated disc. In some embodiments, the size of cage 12 is selected after trialing, cage 12 is visualized by fluoroscopy and oriented before malleting into intervertebral space. Trialing is utilized to establish a starting point for cage 12 insertion. A trial 1300, as shown in FIG. 5, including a shaft 1308, a bubble level and a sphere 1312 is inserted into one or more intervertebral spaces of the L2-L5 vertebral levels. An angle θ of trial 1300 is adjusted until θ equals angle α. Trial 1300 is visualized in the anterior plane and the lateral plane to adjust sphere 1312 position to a center of the disc space while maintaining angle θ. An intersection of shaft 1308 and the vertebral body is marked by point 1350. Marked point 1350 is a starting point for insertion of cage 12 at an angle θ. In some embodiments, the inserter 1400 (see FIG. 6) may also be equipped with a bubble level 1310 or inclinometer such that the insertion angle substantially matches the angle θ determined in the trialing step.

Figure 5A:
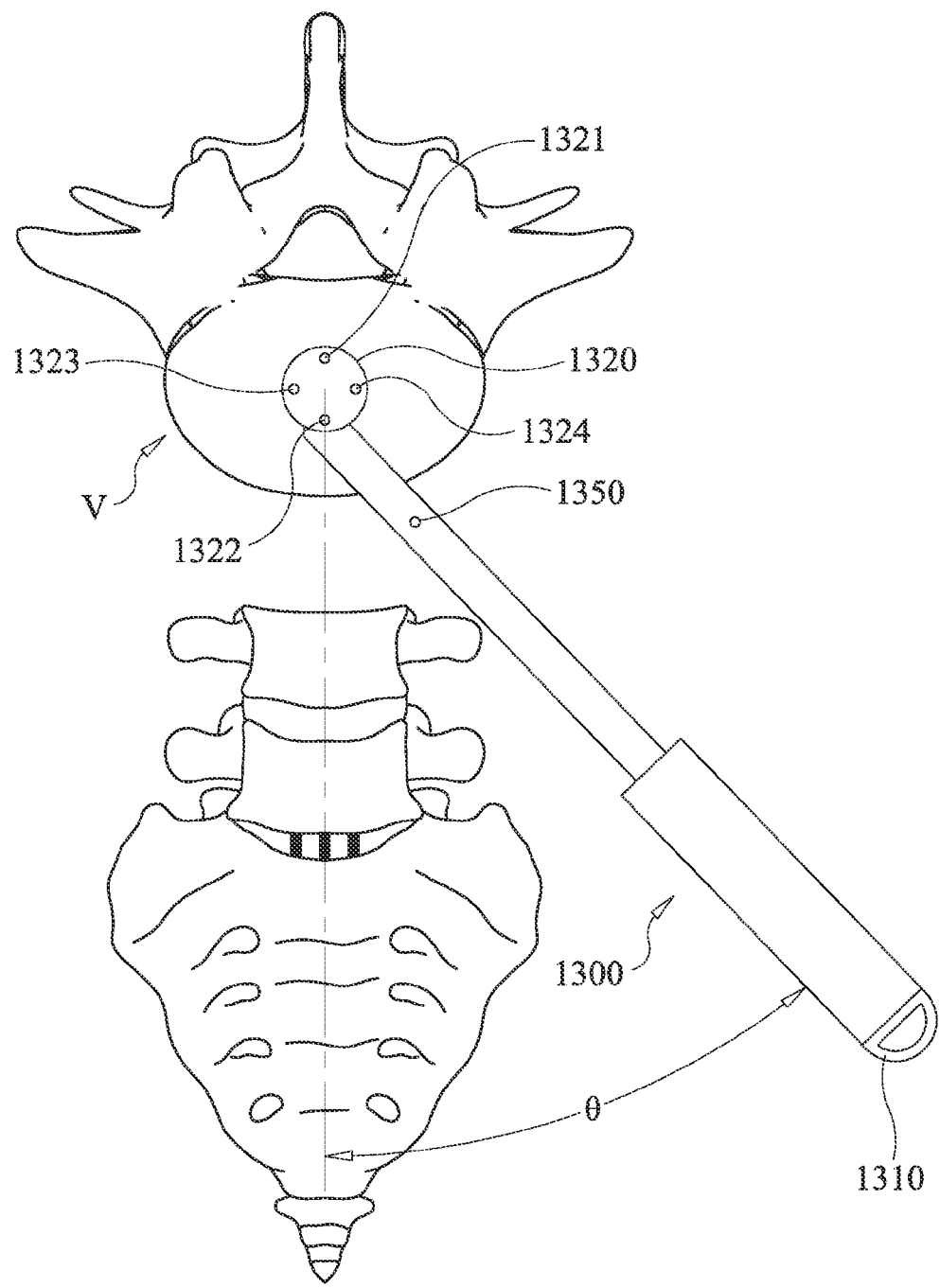
FIG. 5A is a perspective view of components of one embodiment of a system in accordance with the principles of the present disclosure.

An alternative trialing embodiment is shown in FIG. 5A, the trial 1300 includes a cylindrical head 1320 including one or more radiographic markers 1321, 1322, 1323, 1324 (such as, for example, tantalum pins). Those markers 1321, 1322, 1323, 1324 could also be used to help align the shaft of the trial 1300 in the correct angle (i.e. when the markers are in the center of the vertebral body V in both anteroposterior (AP) and lateral radiographic images, and the near and far markers are aligned). The angle of the trial 1300 shaft may be verified as correct and that position can then be marked (see element 1350) on the vertebral body V to be used when the implant 12 in inserted. With the trial 1300 shown in FIG. 20, the bubble level 1310 may not be necessary to obtain the correct angle θ. In order to place the cage 12 in the correct the surgeon need only to center the cage 12 in the vertebral body V and align the mark on the inserter 1400 shaft with the mark 1350 on the vertebral body V. This would eliminate the need for the bubble level 1310 or inclinometer on the inserter 1400 (see FIG. 6). In some embodiments, the trialing instruments of FIGS. 5 and 20 may also be equipped with navigation emitter structures 1410, 1411 (as shown generally in the inserter 1400 instrument of FIG. 6) to allow for compatibility with surgical navigation apparatus as further described herein.

Pilot holes or the like are made in selected vertebra V1, V2 of vertebrae V adjacent the L2-L5 intervertebral space, via surgical pathway P, as shown in FIG. 1, for receiving bone fasteners 42, as shown in FIG. 8. An inserter 1400, as shown in FIG. 6, is attached with cage 12. Inserter 1400 delivers cage 12 through incision I1 and/or incision I2 along surgical pathway P adjacent to a surgical site for implantation adjacent one or more intervertebral spaces of the L2-L5 vertebral levels.

In one embodiment, as shown in FIG. 8, inserter 1400 includes image guidance and/or surgical navigation to monitor, maintain, adjust and/or confirm disposal, delivery and/or alignment of the components of system 10 along surgical pathway P and/or adjacent to a surgical site. For example, the surgical navigation components of system 10 facilitate placement of cage 12 with an intervertebral space of the L2-L5 vertebral levels. The surgical navigation components of system 10 include an emitter 1410 configured to generate a signal representative of a position of inserter 1400 and/or cage 12 connected therewith, for example, along surgical pathway P and/or adjacent to a surgical site such as an intervertebral space of the L2-L5 vertebral levels. In some embodiments, emitter 1410 may include one or a plurality of emitters. In one embodiment, emitter 1410 is shaped substantially like the Greek letter pi and comprises four spaced apart emitters 1411, for generating a signal representing the trajectory of inserter 1400 and/or cage 12 relative to a portion of a patient's anatomy and the depth of inserter 1400 and/or cage 12 along surgical pathway P and/or adjacent to a surgical site. In one embodiment, emitter 1410 includes at least one light emitting diode. In some embodiments, emitter 1410 may include other tracking devices capable of being tracked by a corresponding sensor array, such as, for example, a tracking device that actively generates acoustic signals, magnetic signals, electromagnetic signals, radiologic signals. In some embodiments, emitter 1410 may be removably attached to inserter 1400. In some embodiments, emitter 1410 may be integrally formed with inserter 1400 such that inserter 1400 is a monolithic, unitary body.

In some embodiments, system 10 includes a tracking device (not shown) having an emitter array including one or a plurality of emitters that generate signals representing the position of various body reference points of the patient's anatomy. A sensor (not shown) receives signals from emitter 1410 and the array. The sensor communicates with a processor (not shown), such as, for example, a digitizer control unit, which processes the signals from emitter 1410 and the array to provide information regarding the trajectory of inserter 1400 and/or cage 12 relative to a portion of the patient's anatomy and the depth of inserter 1400 and/or cage 12 along surgical pathway P and/or adjacent to a surgical site. The processor sends this information to a monitor, which provides a visual representation of the position of inserter 1400 and/or cage 12 along surgical pathway P and/or adjacent to a surgical site to allow the medical practitioner to guide inserter 1400 and/or cage 12 to a desired location within the patient's anatomy.

The monitor is configured to generate an image from a data set stored in a controller, such as, for example, a computer. In some embodiments, the data set may be generated preoperatively using scanning techniques, such as, for example, a CAT scanner or MRI scanner. The image data set includes reference points for at least one body part, such as, for example, the spine of a patient, which have a fixed spatial relation to the body part. The processor is connected to the monitor, under control of the computer, and to inserter 1400 and/or cage 12.

The sensor receives and triangulates signals generated by emitter 1410 and the array to identify the relative position of each of the reference points and inserter 1400 and/or cage 12. The processor and the computer modify the image data set according to the identified relative position of each of the reference points during the procedure. The position and trajectory of inserter 1400 and/or cage 12 provided by emitter 1410 and the array is processed by the processor and the computer and is visually displayed against the preoperative image data set stored in the computer to provide the medical practitioner with a visual representation of the trajectory of inserter 1400 and/or cage 12 relative to a portion of the patient's anatomy and the depth of inserter 1400 within the patient's anatomy. See, for example, similar surgical navigation components and their use as described in U.S. Pat. Nos. 6,021,343, 6,725,080, 6,796,988, the entire contents of each of these references being incorporated by reference herein. Emitter 1410 may be tracked using a variety of surgical navigation systems serving as the tracking device, these systems include, but are not limited to the O-Arm® imaging device and StealthStation® surgical navigation device available from Medtronic®, Inc. In addition, emitters 1410 may be applied to a variety of instruments in the present disclosure in order to guide and/or check the proper oblique trajectory. Emitter 1410 navigated instruments may include, but are not limited to: cage inserters (see FIG. 6), trials 1300 (see FIG. 5), driver instruments for fasteners 42a (see FIG. 12B), probes, discectomy instruments, and/or combinations of such instruments, such as an inserter with integrated screw trajectory guides.

Anterior surface 14 faces an anterior side of body B adjacent anterior portion A1 and posterior surface 16 faces a posterior side of body B, as described herein. Surface 18 engages endplate tissue of endplate E1 and surface 20 engages endplate tissue of endplate E2. Screw holes 24, 26 are oriented with the body of cage 12 in substantial alignment with surgical pathway P, as described herein. Screw hole 24 is oriented to receive a fastener 42a via surgical pathway P and is disposed at an angular orientation such that fastener 42a is delivered to the intervertebral space via surgical pathway P and oriented to penetrate endplate tissue of endplate E1, as shown in FIG. 1. Opening 46 guides fastener 42a into screw hole 24 relative to axis XL and in substantial alignment with surgical pathway P. Screw hole 26 is oriented to receive a fastener 42b via surgical pathway P and is disposed at an angular orientation such that fastener 42b is delivered to the intervertebral space via surgical pathway P and oriented to penetrate endplate tissue of endplate E2, as shown in FIGS. 1 and 8. Opening 48 guides fastener 42b into screw hole 26 relative to axis XL and in substantial alignment with surgical pathway P. A driver (not shown) is disposed adjacent the intervertebral space and is manipulated to drive, torque, insert or otherwise connect bone fasteners 42a, 42b adjacent the intervertebral space. In some embodiments, the driver may include surgical navigation components, as described herein, to establish a screw pathway that is substantially concurrent with and/or parallel to the surgical approach angle.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft allograft, xenograft, autograft, bone paste, bone chips, Skelite®, and/or bone morphogenetic protein (BMP) to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration. The various cage 12, 212, 312, 412 embodiments described herein may also be coated with a variety of substances to promote bone ingrowth or ongrowth, including but not limited to titanium and hydroxyapatite (HA). In such embodiments, titanium coatings may be applied via a variety of methods, including but not limited to plasma spray coating and/or mechanical attachment of titanium plates to form a PEEK/Titanium implant.

Figure 9:
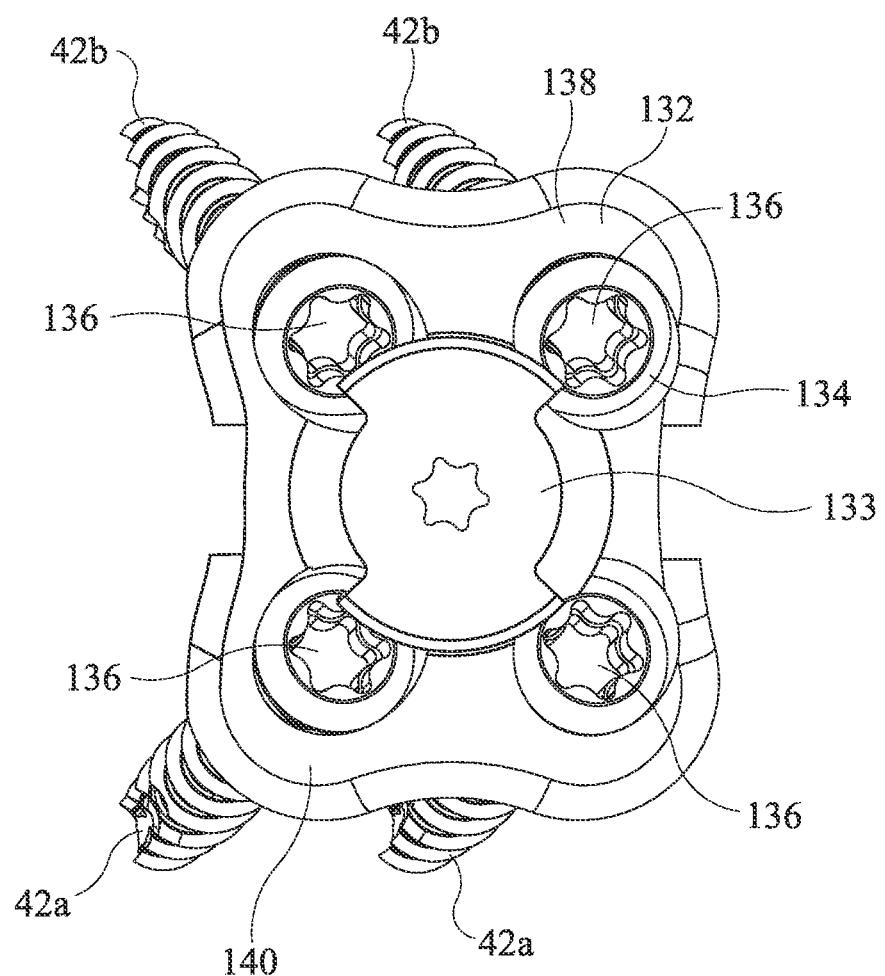
FIG. 9 is a perspective view of components of one embodiment of a system in accordance with the principles of the present disclosure.
Figure 10:
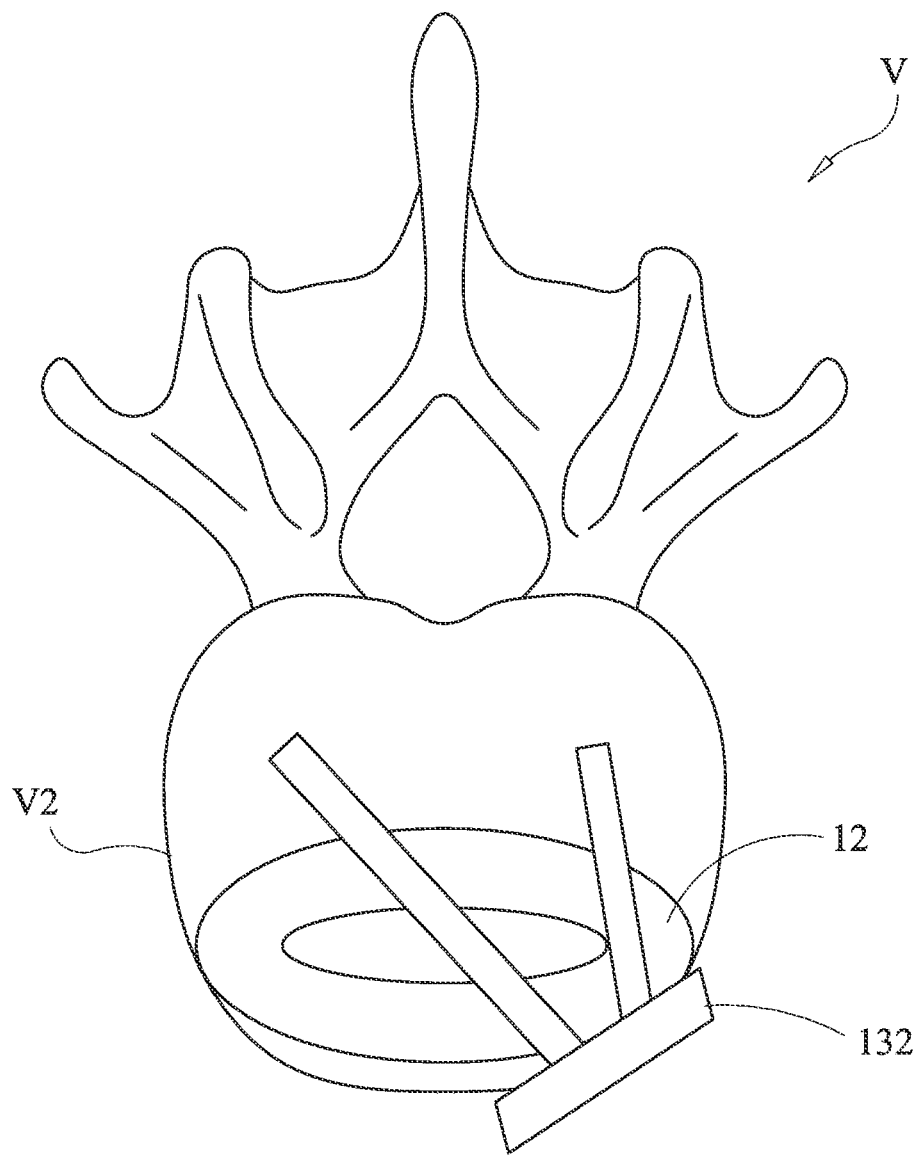
FIG. 10 is a plan view of components of one embodiment of a system in accordance with the principles of the present disclosure.

In one embodiment, as shown in FIGS. 9 and 10, system 10, similar to the systems and methods described herein, comprises a spinal construct including cage 12, described above, and a plate 132 delivered through incision 11 and/or 12 along surgical pathway P, as described herein, adjacent to a surgical site for implantation adjacent one or more intervertebral spaces of the L2-L5 vertebral levels, as shown in FIG. 10. Plate 132 includes a portion 138 configured to engage a vertebral level V1 and a portion 140 configured to engage a vertebral level V2. In one embodiment, plate 132 may be attached with cage 12 prior to implantation or in situ. Plate 132 includes an inner surface 134 that defines openings 136 configured to receive fasteners 42, described herein. Fasteners 42*a* are configured for fixation with vertebral level V2 and fasteners 42*b* are configured for fixation with vertebral level V1. In one embodiment, plate 132 is secured with cage 12 via a fastener. In some embodiments, plate 132 includes a back out prevention element 133.

Figure 16:
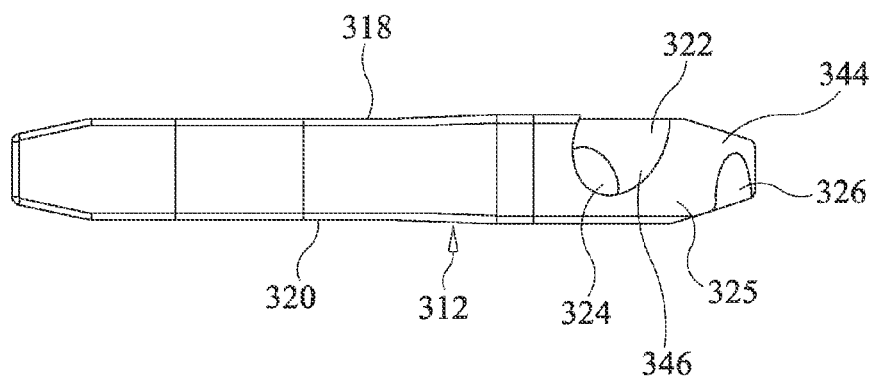
FIG. 16 is a perspective view of a component of one embodiment of a system in accordance with the principles of the present disclosure.

In one embodiment, as shown in FIGS. 11-15A, system 10, similar to the systems and methods described herein, may comprise a cage 212, 312 similar to cage 12 described above. More particularly, cage 312 (shown generally in FIGS. 13, 14 and 16) may provide a substantially zero-profile cage 312 having a thickness measured between the surfaces 318, 320 that is substantially equivalent over the extent of the cage 312, as shown in FIG. 16. As shown in FIG. 14, cage 312 comprises an oblique portion 344 defining a pair of holes 324, 326 configured for receiving and guiding fasteners 42*a*, 42*b* along a generally oblique angle, such as, for example, α3 and α4 of FIG. 13, into the adjacent endplates, see endplate E2 of the vertebral body V2, into which fastener 42*a* extends in FIG. 14.

Figure 12:
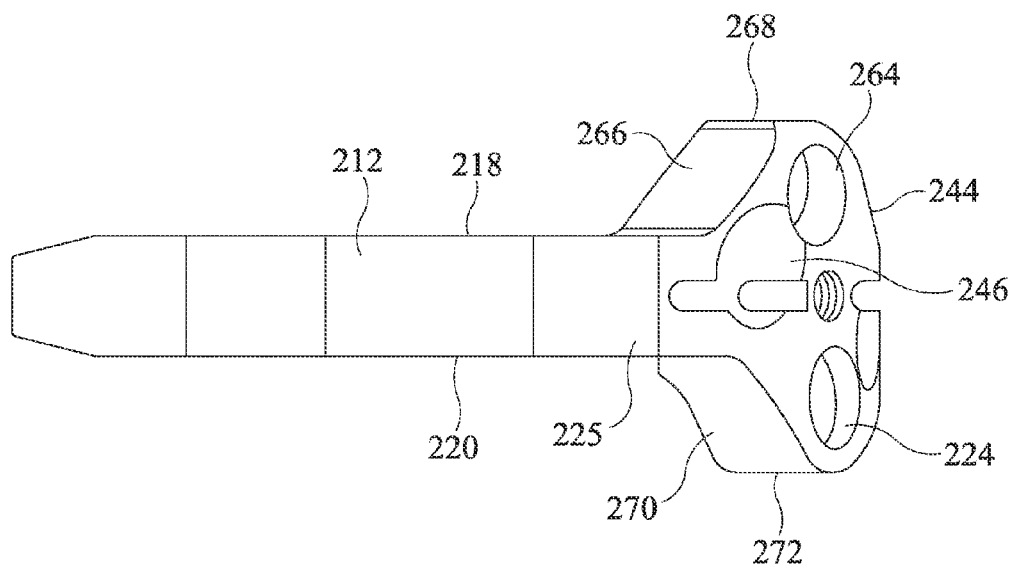
FIG. 12 is an oblique end view of the components shown in FIG. 11.
Figure 12A:
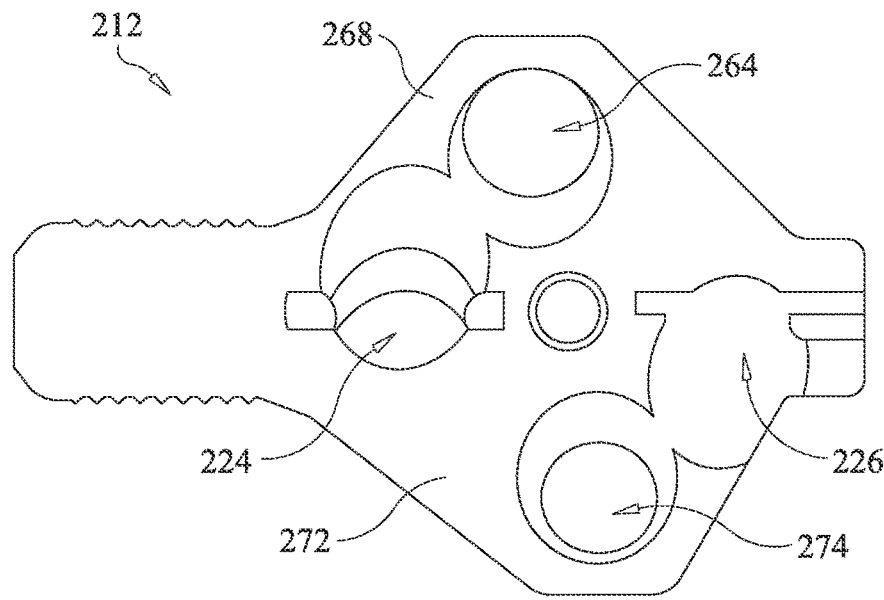
FIG. 12A is an oblique end view of the components shown in FIG. 11.
Figure 12B:
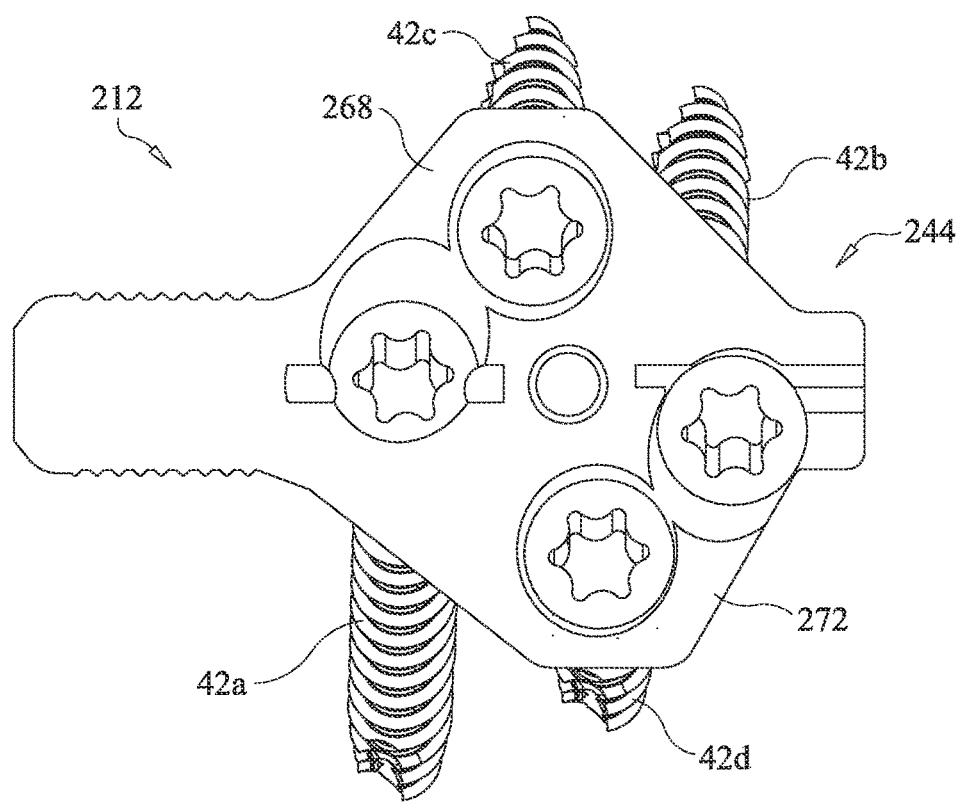
FIG. 12B is a side view of the components shown in FIG. 11 with fasteners.
Figure 12C:
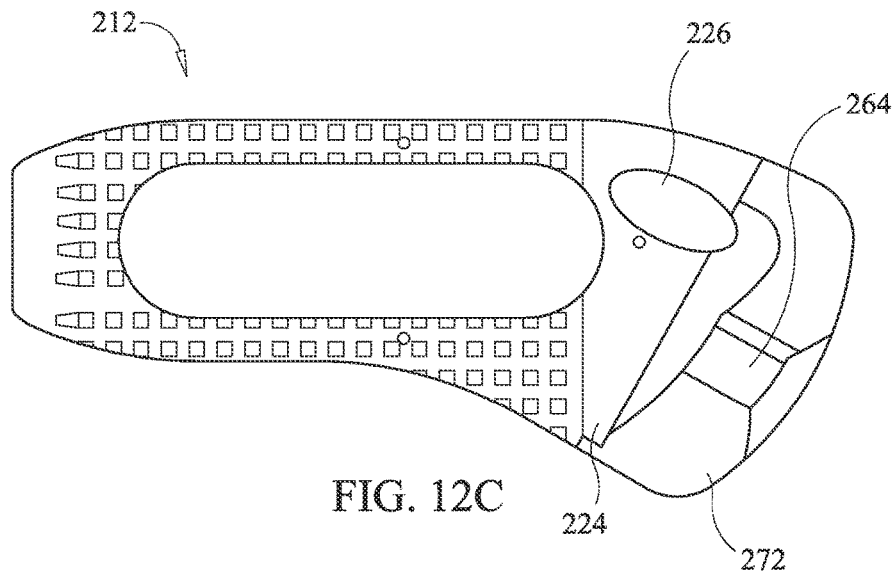
FIG. 12C is a top view of the components shown in FIG. 11.
Figure 12D:
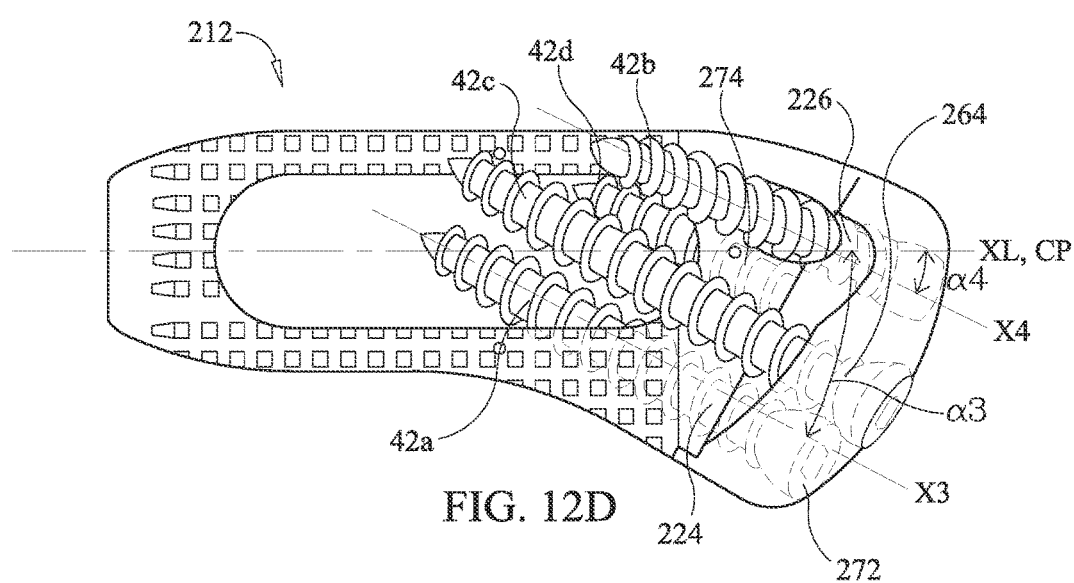
FIG. 12D is a top view of the components shown in FIG. 11 with fasteners.
Figure 15:
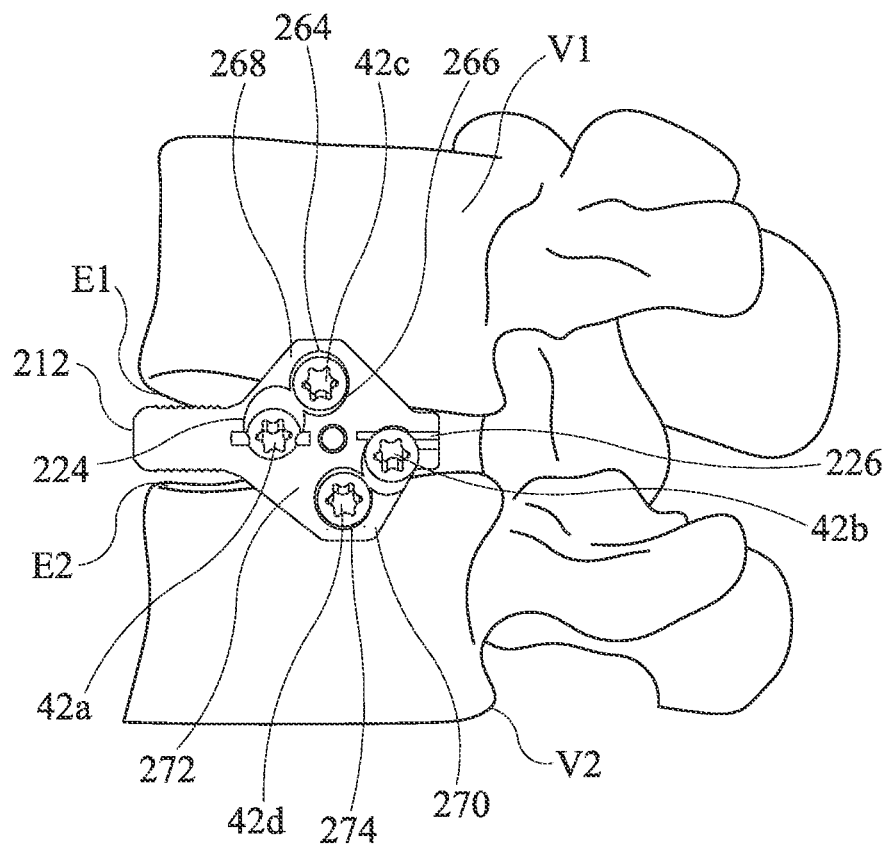
FIG. 15 is a plan view of components shown in FIG. 11 disposed with vertebrae.
Figure 15A:
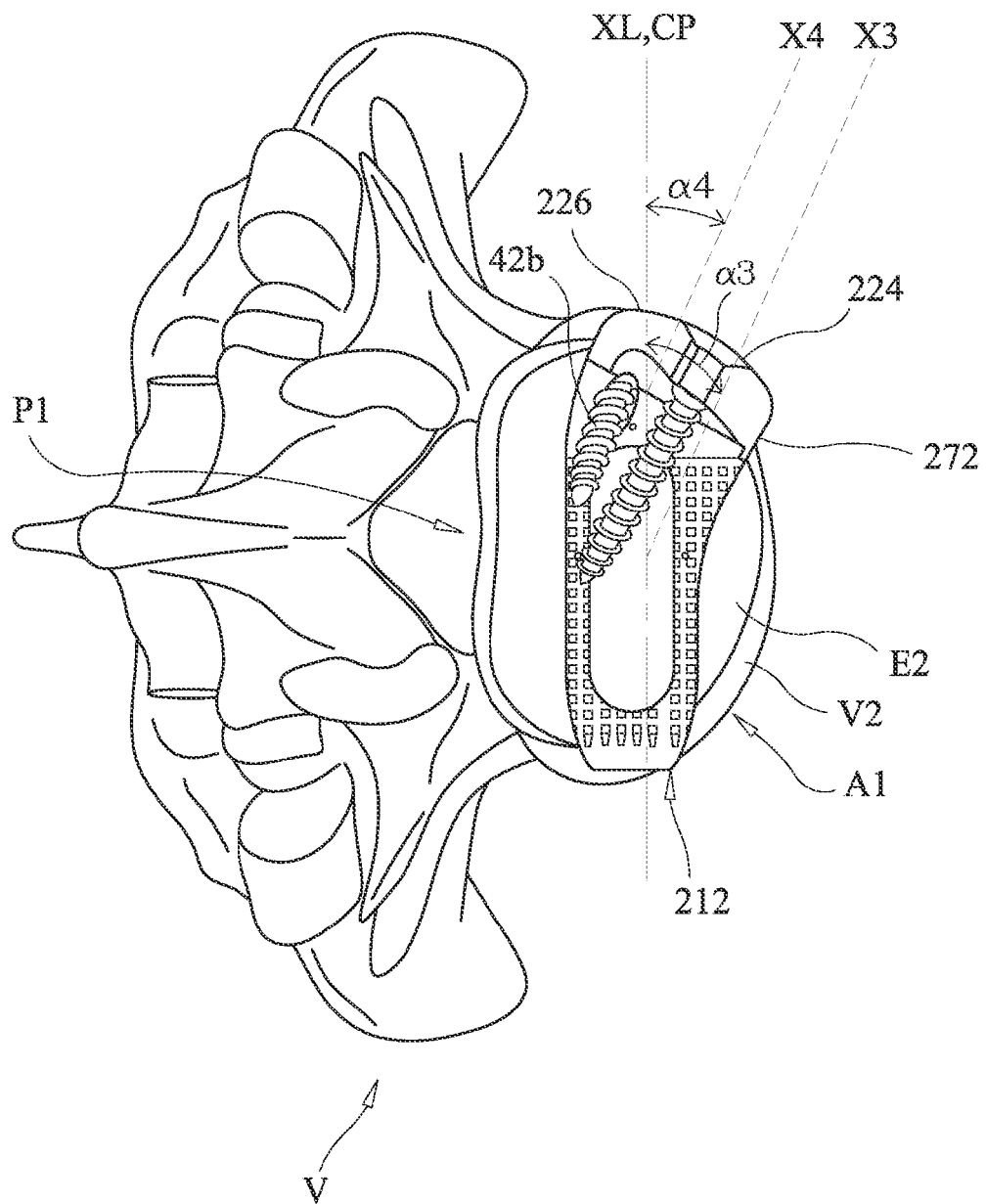
FIG. 15A is a plan view of the components and vertebrae shown in FIG. 15.

Referring now to FIG. 12, cage 212 is shown as a "hybrid" flanged implant which is configured to receive and guide a set of 4 fasteners (42*a*, 42*b*, 42*c*, 42*d*) along a generally oblique angle, such as, for example, α3 and α4 of FIG. 15A. More particularly, cage 212 is formed with a flange 272 defining holes (224, 226) for guiding some of the fasteners into the adjacent vertebral endplates (see fasteners 42*a*, 42*b*). The flange 272 (having an oblique surface) may also define outer holes 264, 274 defined and oriented to guide other fasteners 42*c*, 42*d* into side walls of adjacent vertebral bodies (V1 and V2, as shown in FIG. 15).

Figure 17:
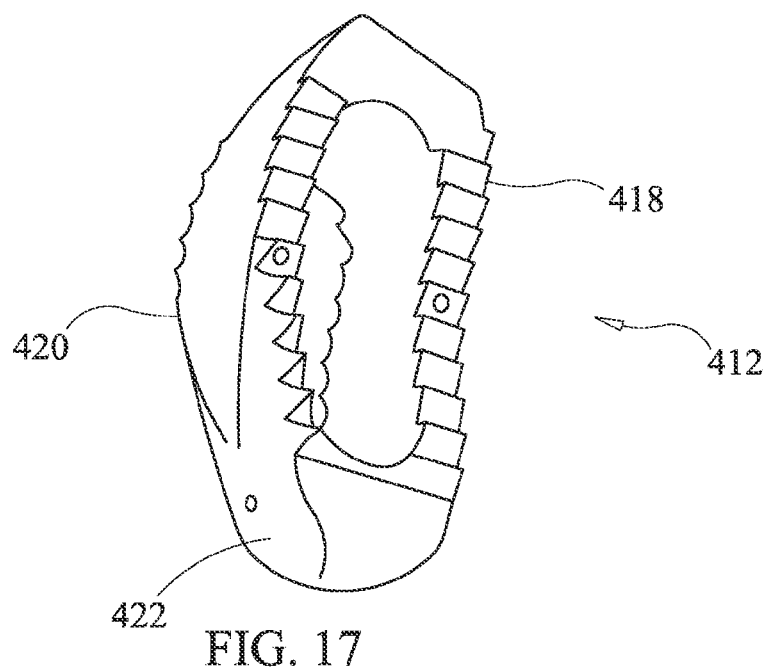
FIG. 17 is a perspective view of components of one embodiment of a system in accordance with the principles of the present disclosure.
Figure 18:
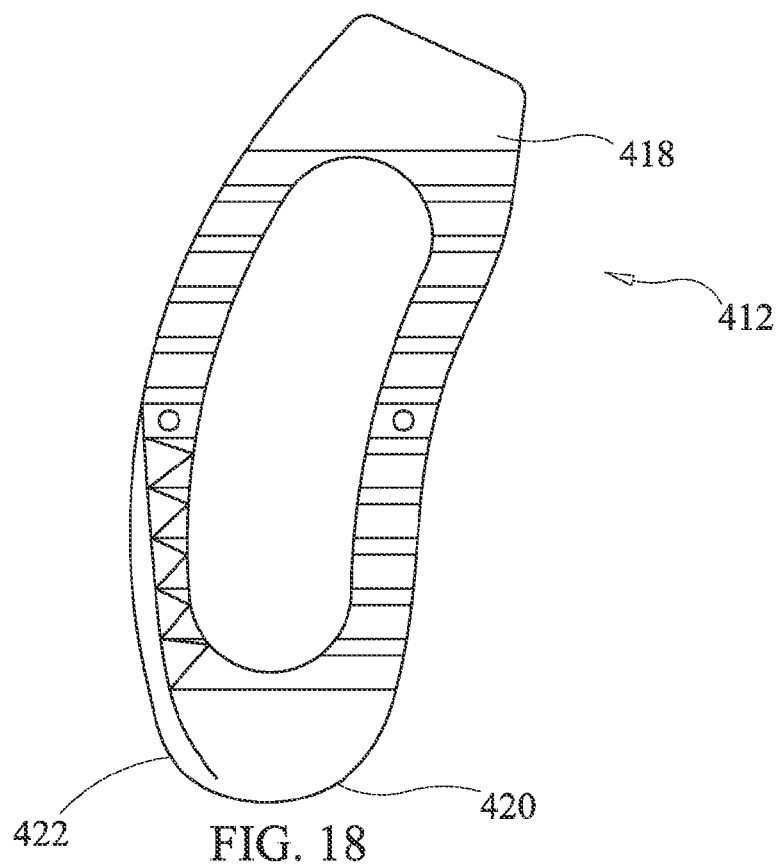
FIG. 18 is a top view of components shown in FIG. 17.
Figure 19:
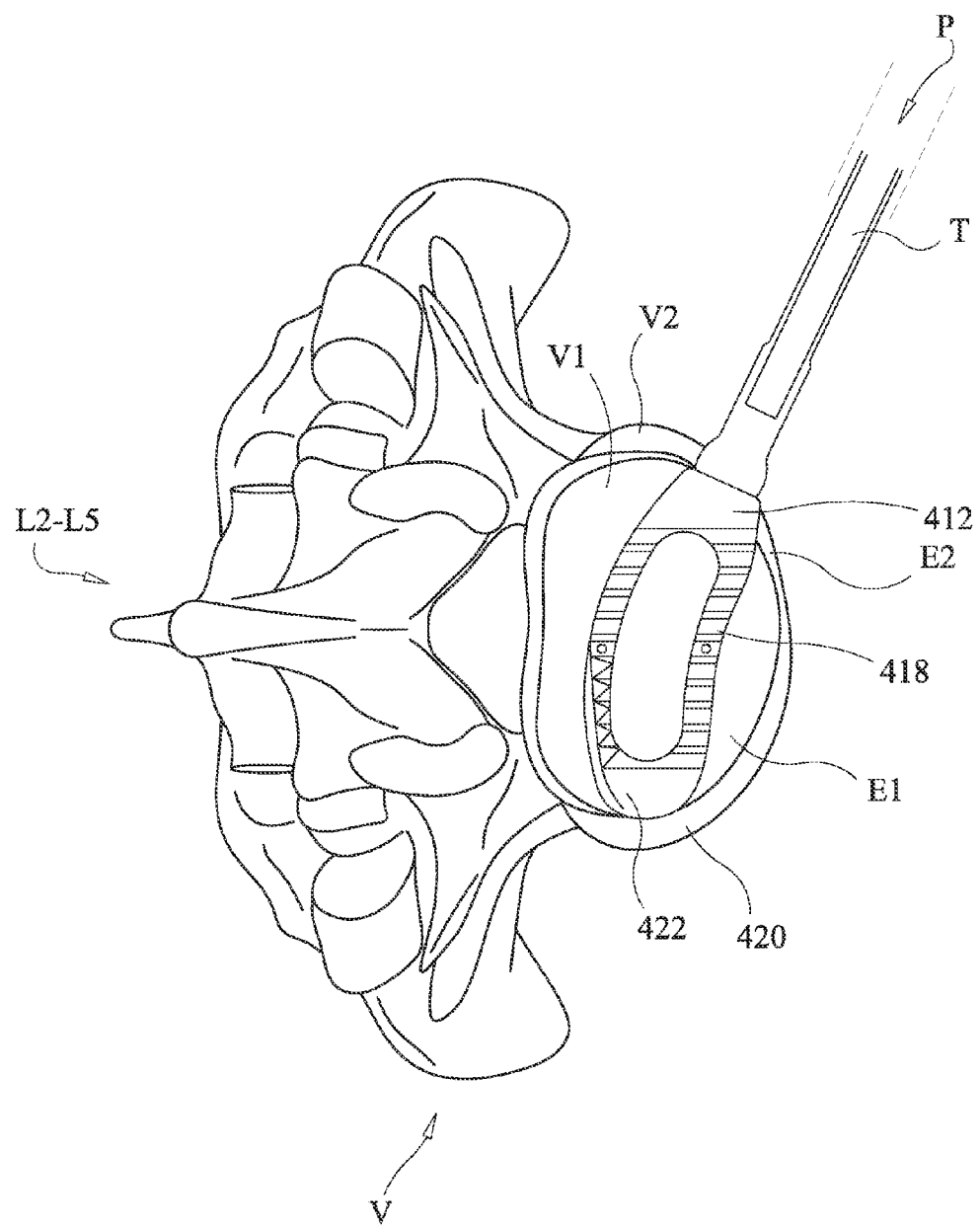
FIG. 19 is a plan view the components shown in FIG. 17 disposed with vertebrae.

Referring generally to FIGS. 11, 12, 12A, 12B, and 15, cage 212 extends between an anterior surface 214 and a posterior surface 216. Anterior surface 214 is configured to face an anterior side of body B and be disposed adjacent an anterior portion of vertebrae, such as, for example an anterior portion A1 of one or more intervertebral spaces of the L2-L5 vertebral levels of vertebrae V. Posterior surface 216 is configured to face a posterior side of body B and be disposed adjacent a posterior portion of vertebrae, such as, for example a posterior portion P1 of one or more intervertebral spaces of the L2-L5 vertebral levels of vertebrae V. In some embodiments, surface 216 includes an angled surface 216*a* that is configured for contouring away from a contralateral foramen. In other embodiments, as shown in FIGS. 17-19, the cage may comprise curved (convex and/or concave anterior and posterior surfaces) to create a more anatomically-compatible cage footprint that may also more easily be placed from an oblique surgical angle as described further herein.

Cage 212 includes a first vertebral engaging surface 218 and a second vertebral engaging surface 220. Surface 218 is configured to engage endplate tissue of a vertebral body, such as, for example, an endplate E1 of a V1 vertebral body, as described herein. Surface 220 is configured to engage endplate tissue of a vertebral body, such as, for example, an endplate E2 of a V2 vertebral body, as shown in FIG. 15A. Surfaces 218, 220 may be substantially planar in some embodiments. In some embodiments, surfaces 218, 220 may comprise chamfers, radii or other features to aid in insertion and placement between vertebral bodies. Surfaces 218, 220 may also be provided with convexity along the length and/or width of the cage 212 so as to conform to complementary surfaces of the vertebral endplates with which they may be engaged.

Figure 11A:
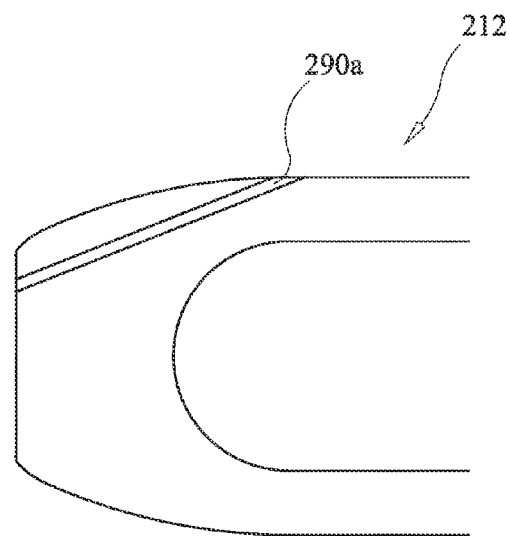
FIG. 11A is a plan view of components of one embodiment of a system in accordance with the principles of the present disclosure.

Cage 212 may be provided with a substantially rectangular cross section configuration and includes an inner surface 222 that defines an opening 223 configured to receive an agent, which may include bone graft (not shown) and/or other materials, as described herein, for employment in a fixation or fusion treatment. In some embodiments cage 212 includes radiopaque markers 290 to facilitate positioning of cage 212 and indicate location of a contralateral edge, a leading nose, and a posterior wall of cage 212. In some embodiments, cage 212 includes linear markers 294 configured to indicate a position of an angled surface away from a contralateral foramen. In one embodiment, as shown in FIG. 11A, cage 212 includes an angled radiopaque marker 290*a*, which provides visual indicia of positioning of the contralateral edge of cage 212, such as, for example, surface 216*a* and/or a leading nose position and a posterior wall with the ends of marker 290*a*.

Inner surface 222 includes internally threaded and/or non-threaded portions that define a screw hole 224 and a screw hole 226. Screw hole 224 extends along the body of cage 212 in a transverse configuration relative to the surfaces of cage 212, described herein, for fixation with tissue. Screw hole 224 is oriented with the body of cage 212 in substantial alignment with oblique surgical pathway P formed in body B, as described herein.

Figure 13:
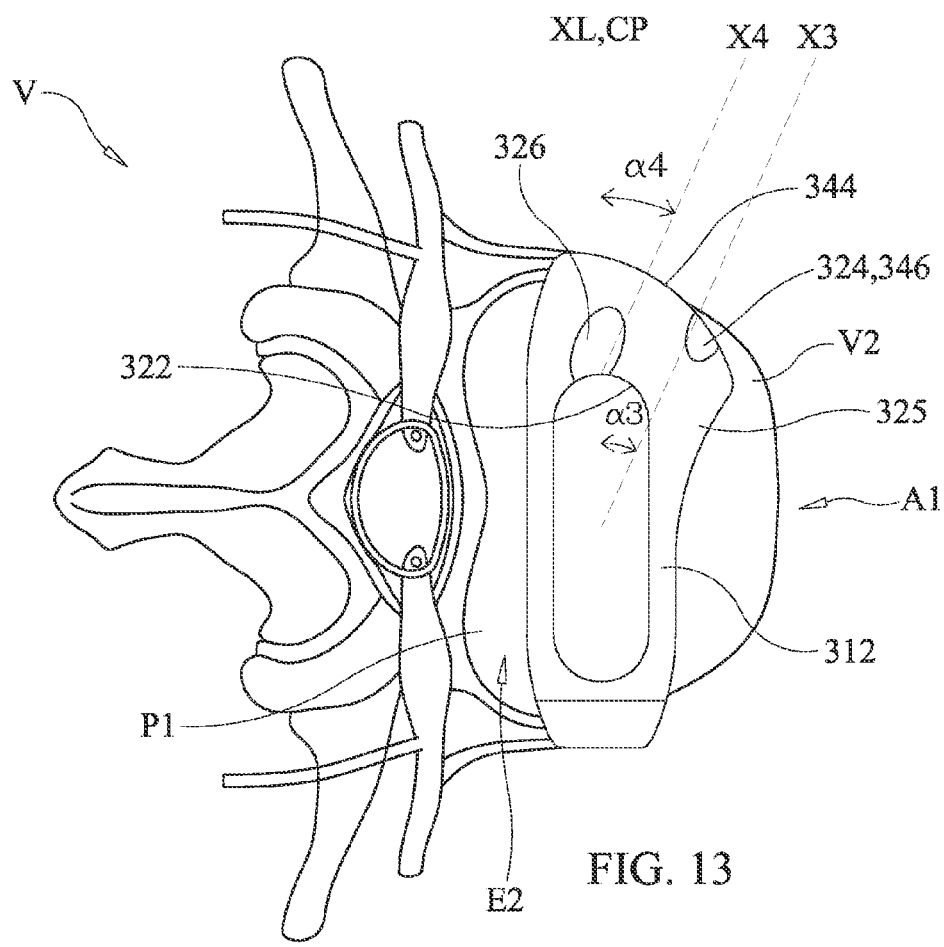
FIG. 13 is a plan view of the components shown in FIG. 16 disposed with vertebrae.

Screw hole 224 defines an axis X3 oriented oblique relative to axis XL, described herein, such that screw hole 224 implants a fastener, as described herein, oblique relative to axis XL and adjacent portion A1. Axis XL lies in plane CP defined by body B in substantial alignment with one or more intervertebral spaces of the L2-L5 vertebral levels, as shown in FIG. 13.

Axis X3 is disposed in substantial alignment with surgical pathway P and at an oblique angle α3 relative to axis XL. In some embodiments, angle α3 is in a range of approximately 0-45 degrees. In one embodiment, angle α3 is oriented approximately 15-30 degrees relative to axis XL and substantially aligned with surgical pathway P such that screw hole 224 is configured to receive a fastener via surgical pathway P. In some embodiments, screw hole 224 is also disposed at an angular orientation relative to plane CP and/or axis XL such that a fastener is delivered to a surgical site including one or more intervertebral spaces of the L2-L5 vertebral levels via surgical pathway P and oriented to penetrate endplate tissue of a vertebral body, such as, for example, an endplate E2. In some embodiments, screw hole 224 and/or the body of cage 212 may be disposed at an angular orientation relative to plane CP and/or axis XL such that a fastener is oriented to penetrate endplate tissue of a vertebral body.

Screw hole 226 extends along the body of cage 212 in a transverse configuration relative to the surfaces of cage 212, described herein, for fixation with tissue. Screw hole 226 is oriented with the body of cage 212 in substantial alignment with surgical pathway P. In some embodiments, substantial alignment of all or only a portion of screw hole 226 with all or only a portion of surgical pathway P includes co-axial, spaced apart, offset, angularly offset and/or parallel alignment.

Screw hole 226 defines an axis X4 oriented oblique relative to axis XL such that screw hole 226 implants a fastener, as described herein, oblique relative to axis XL and adjacent portion A1. Axis X4 is disposed in substantial alignment with surgical pathway P and at an oblique angle α4 relative to axis XL. In some embodiments, angle α4 is in a range of approximately 0-45 degrees. In one embodiment, angle α4 is oriented approximately 15-30 degrees relative to axis XL and substantially aligned with surgical pathway P such that screw hole 226 is configured to receive a fastener via surgical pathway P. In some embodiments, screw hole 226 is also disposed at an angular orientation relative to plane CP and/or axis XL such that a fastener is delivered to a surgical site including one or more intervertebral spaces of the L2-L5 vertebral levels via surgical pathway P and oriented to penetrate endplate tissue of a vertebral body such as, for example, endplate E1. In some embodiments, screw hole 226 and/or the body of cage 212 may be disposed at an angular orientation relative to plane CP and/or axis XL such that a fastener is oriented to penetrate endplate tissue of a vertebral body. In some embodiments, angle α3 and/or α4 may be equal, substantially equivalent and/or different. In some embodiments, surgical pathway P, axis X3 and/or axis X4 may be co-axial, spaced apart, offset, angularly offset and/or parallel alignment.

Outer surface 225 includes an oblique surface, such as, for example, a flange 244 that defines an opening 246 disposed in communication and substantial alignment with screw hole 224. Flange 244 is oriented with cage 212 and in substantial alignment with surgical pathway P. Opening 246 is configured to guide a fastener into screw hole 224 relative to axis XL and in substantial alignment with surgical pathway P. In some embodiments, flange 244 is configured for mating engagement with a surgical instrument, such as, for example, an inserter, which delivers cage 212 adjacent a surgical site via surgical pathway P, as described herein.

In some embodiments, flange 244 is configured for fixed disposal with cage 212 and can be monolithically formed therewith. In some embodiments, flange 244 is configured for moveable disposal with cage 212 such that flange 244 is selectively removable from a portion of cage 212 to facilitate placement within the intervertebral space. In some embodiments, flange 244 includes a surface that may be rough, textured, porous, semi-porous, dimpled and/or polished.

In one embodiment, the oblique surface includes a surface 266 including a flange 268 and a surface 270 including a flange 272. Range 268 is configured to engage a side wall of vertebrae V1 and includes screw hole 264. Screw hole 264 is oriented with the body of cage 212 in substantial alignment with oblique surgical pathway P formed in body B, similar to that described herein. Screw hole 264 defines an axis oriented oblique relative to axis XL, described herein, such that screw hole 264 implants a fastener, as described herein, oblique relative to axis XL.

Flange 272 is configured to engage a side wall of vertebrae V2 and includes a screw hole 274. Screw hole 274 is oriented with the body of cage 212 in substantial alignment with oblique surgical pathway P formed in body B, similar to that described herein. Screw hole 274 defines an axis oriented oblique relative to axis XL, described herein, such that screw hole 274 implants a fastener, as described herein, oblique relative to axis XL.

Screw hole 264 is configured to receive fastener 42c, similar to fasteners 42 described herein, to attached cage 212 to a side wall of vertebrae V1. Screw hole 274 is configured to receive fastener 42d, similar to fasteners 42 described herein, to attached cage 212 to a side wall of vertebrae V2. Spinal implant system 10 includes one or more fasteners 42, as shown in FIGS. 14-15A, for attaching cage 212 with tissue, as described herein. In some embodiments, the oblique surface extends to an anterior corner of cage 212 to allow for easier access to screws along surgical pathway P when cage 212 is in its final/lateral position with an intervertebral space.

In assembly, operation and use, as shown in FIGS. 13-15A, spinal implant system 10, similar to the systems and methods described herein, is employed with a surgical procedure for treatment of a spinal disorder, such as those described herein, affecting a section of a spine of a patient. Pilot holes or the like are made in selected vertebra V1, V2 of vertebrae V adjacent one or more intervertebral spaces of the L2-L5 vertebral levels, via surgical pathway P, for receiving bone fasteners 42a, 42b, 42c, 42d. An inserter (not shown), attached with cage 212, delivers cage 212 through incision 11 and/or incision 12 along surgical pathway P adjacent to a surgical site for implantation adjacent the intervertebral space. Anterior surface 214 faces an anterior side of body B adjacent anterior portion A1 and posterior surface 216 faces a posterior side of body B, as described herein. Surface 218 engages endplate tissue of endplate E1 and surface 220 engages endplate tissue of endplate E2.

Screw holes 224, 226, 264, 274 are oriented with the body of cage 212 in substantial alignment with surgical pathway P, as described herein. Screw hole 224 is oriented to receive a fastener 42a via surgical pathway P and is disposed at an angular orientation such that fastener 42a is delivered to the intervertebral space via surgical pathway P and oriented to penetrate endplate tissue of endplate E2, as shown in FIGS. 14-15. Opening 246 guides fastener 42a into screw hole 224 relative to axis XL and in substantial alignment with surgical pathway P.

Screw hole 226 is oriented to receive a fastener 42b via surgical pathway P and is disposed at an angular orientation such that fastener 42b is delivered to the intervertebral space via surgical pathway P and oriented to penetrate endplate tissue of endplate E1, as described herein. Opening 248 guides fastener 42b into screw hole 226 relative to axis XL and in substantial alignment with surgical pathway P.

Screw hole 264 is oriented to receive a fastener 42c via surgical pathway P and is disposed at an angular orientation such that fastener 42c is delivered to the surgical site via surgical pathway P and oriented to penetrate sidewall tissue of vertebra V1, as described herein. Screw hole 264 guides fastener 42c into sidewall tissue of vertebra V1 relative to axis XL and in substantial alignment with surgical pathway P. Screw hole 274 is oriented to receive a fastener 42d via surgical pathway P and is disposed at an angular orientation such that fastener 42d is delivered to the surgical site via surgical pathway P and oriented to penetrate sidewall tissue of vertebra V2, as described herein. Screw hole 274 guides fastener 42d into sidewall tissue of vertebra V2 relative to axis XL and in substantial alignment with surgical pathway P.

A driver (not shown) is disposed adjacent the L2-L5 intervertebral space and is manipulated to drive, torque, insert or otherwise connect bone fasteners 42a, 42b, 42c, 42d adjacent the intervertebral space. Upon completion of a procedure, as described herein, the surgical instruments, assemblies and non-implanted components of spinal implant system 10 are removed and the incision(s) are closed.

In one embodiment, as shown in FIG. 16, system 10, similar to the systems and methods described herein, comprises a spinal construct including a cage 312, similar to cage 12 discussed herein. Cage 312 includes a flat profile configuration. Cage 312 includes a first vertebral engaging surface 318 and a second vertebral engaging surface 320.

Inner surface 322 includes internally threaded and/or non-threaded portions that define a screw hole 324 and a screw hole 326, similar to screw holes 24, 26 described herein. Screw hole 324 extends along the body of cage 312 in a transverse configuration relative to the surfaces of cage 312, described herein, for fixation with tissue. Screw hole 324 is oriented with the body of cage 312 in substantial alignment with an oblique surgical pathway P formed in body B, as described herein. Outer surface 325 includes an oblique surface 344 that defines an opening 346 disposed in communication and substantial alignment with screw hole 324, similar to the spinal constructs described herein.

In one embodiment, as shown in FIGS. 17-19, similar to the systems and methods described herein, comprises a spinal construct including a cage 412, similar to cage 12 discussed herein. Cage 412 includes an angled profile configuration. In one embodiment, cage 412 is angled toward pathway P to facilitate insertion. Cage 412 includes a first vertebral engaging surface 418 and a second vertebral engaging surface 420. Cage 412 includes a proximal end 421 that is biased, angled and/or curved toward an oblique approach angle, similar to the surgical pathways described herein. Cage 412 includes a posterior, contralateral wall 422 bulleting that facilitates insertion along an oblique surgical pathway. In one embodiment, wall 422 is smooth such that there are no sharp edges near posterior nerve roots thereby reducing damage to the nerves.

In assembly, operation and use, as shown in FIG. 19, spinal implant system 10, similar to the systems and methods described herein, is employed with a surgical procedure for treatment of a spinal disorder, such as those described herein, affecting a section of a spine of a patient. Pilot holes or the like are made in selected vertebra V1, V2 of vertebrae V adjacent one or more intervertebral spaces of the L2-L5 vertebral levels, via surgical pathway P, for receiving bone fasteners. An inserter T is attached with cage 412, and delivers cage 412 through an incision along surgical pathway P adjacent to a surgical site for implantation adjacent the intervertebral space. Surface 418 engages endplate E1 and surface 420 engages endplate E2. In some embodiments, cage 412 may be obliquely inserted and an inserter is attached and manipulated along an oblique surgical pathway as described herein to come through the oblique access such that cage 412 is inserted obliquely. In some embodiments, cage 412 is orthogonally inserted and the inserter is attached orthogonally to allow a direct lateral insertion or orthogonal move from the oblique surgical pathway.

The components of cages 12, 212, 312, 412 can be fabricated from a variety of biologically acceptable materials suitable for medical applications, including metals, synthetic polymers, ceramics and bone material and/or their composites, depending on the particular application and/or preference of a medical practitioner. For example, the components of cages 12, 212, 312, 412, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyether-ketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

It will be understood that various modifications and/or combinations may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
an implant body including opposite top and bottom surfaces, an anterior surface and an opposite posterior surface, the anterior and posterior surfaces each extending between the top and bottom surfaces, the implant body including an oblique wall that extends from the anterior surface to the posterior surface,
wherein the oblique wall includes an inner surface defining a screw hole that extends through opposite inner and outer surfaces of the oblique wall such that no portion of the screw hole extends through the top surface or the bottom surface, the screw hole being oriented to implant a fastener oblique relative to a lateral axis of a subject body and adjacent an intervertebral space of the subject body.

2. A spinal implant as recited in claim 1, wherein the oblique wall includes a flange that is inferior to the bottom surface, the screw hole extending through the flange.

3. A spinal implant as recited in claim 2, wherein the flange is monolithically formed with the implant body.

4. A spinal implant as recited in claim 1, wherein the oblique wall includes a first flange that is superior to the top surface and configured to engage a first vertebra and a second flange that is inferior to the bottom surface and configured to engage a second vertebra.

5. A spinal implant as recited in claim 1, wherein the oblique wall comprises a second screw hole that extends through the inner and outer surfaces such that the second screw hole is spaced apart from the top surface, the bottom surface and the screw hole, the screw holes each being figured to guide fasteners at selected angles relative to the lateral axis.

6. A spinal implant as recited in claim 5, wherein the implant body includes a third screw hole that extends through the oblique wall and the top surface and a fourth screw hole that extends through the oblique wall and the bottom surface.

7. A spinal implant as recited in claim 6, wherein the third screw hole is in substantial alignment with the screw hole and the fourth screw hole is in substantial alignment with the second screw hole.

8. A spinal implant as recited in claim 1, wherein the implant body includes an interbody cage having a plurality of screw holes that guide fasteners at selected angles relative to the lateral axis.

9. A spinal implant as recited in claim 1, wherein the screw hole defines a longitudinal axis disposed at an oblique angle relative to the lateral axis in a range of approximately 0-45 degrees.

10. A spinal implant as recited in claim 1, wherein the screw hole is configured for alignment with an oblique surgical pathway.

11. A spinal implant as recited in claim 1, wherein the screw hole defines a longitudinal axis disposed at an angle of approximately 15-30 degrees relative to the lateral axis and substantially aligned with an oblique surgical pathway such that the screw hole is configured to receive the fastener via the pathway.

12. A spinal implant as recited in claim 1, wherein the implant body comprises an opening that extends through the top and bottom surfaces.

13. A spinal implant as recited in claim 1, wherein the top and bottom surfaces are both planar.

14. A spinal implant as recited in claim 1, wherein the top and bottom surfaces each include a plurality of teeth.

15. A spinal implant as recited in claim 1, wherein the implant body includes a threaded inner surface that defines at least a portion of the screw hole.

16. A spinal implant comprising:
an implant body including opposite top and bottom surfaces, an anterior surface and an opposite posterior surface, the anterior and posterior surfaces each extending between the top and bottom surfaces, the implant body including an opening that extends through the top and bottom surfaces, the implant body including an oblique wall that extends from the anterior surface to the posterior surface, the oblique wall comprising a first flange that is superior to the top surface and a second flange that is inferior to the bottom surface,
wherein the first flange includes a surface defining spaced apart first and screw holes that each extend through opposite inner and outer surfaces of the oblique wall such that no portion of the screw holes extends through the top surface or the bottom surface, the screw holes being oriented to implant a fastener oblique relative to a lateral axis of a subject body and adjacent an intervertebral space of the subject body.

17. A spinal implant as recited in claim 16, wherein the implant body includes a third screw that extends through the oblique wall and the top surface and a fourth screw hole that extends through the oblique wall and the bottom surface.

18. A spinal implant as recited in claim 17, wherein the third screw hole is in substantial alignment with the first screw hole and the fourth screw hole is in substantial alignment with the second screw hole.

19. A spinal implant as recited in claim 17, wherein the implant body includes a first threaded inner surface that defines at least a portion of the third screw hole and a second threaded inner surface that defines at least a portion of the fourth screw hole.

20. A spinal implant comprising:
an implant body extending between an anterior surface and a posterior surface, and including a first vertebral engaging surface and a second vertebral engaging surface,
the implant body further including an inner surface that defines a first screw hole and a second screw hole disposed in substantially parallel alignment, the screw holes being oriented to implant fasteners oblique relative to a lateral axis of a subject body and adjacent an intervertebral space of the subject body such that the implant fasteners are in substantially parallel alignment, and
the implant body further including an oblique surface having a first flange that defines a third screw hole oriented to implant a fastener with a first vertebra and a second flange oriented to implant a fastener with a second vertebra.

* * * * *

UNITED STATES PATENT AND TRADEMARK OFFICE
CERTIFICATE OF CORRECTION

PATENT NO. : 9,918,848 B2
APPLICATION NO. : 14/494381
DATED : March 20, 2018
INVENTOR(S) : Waugh et al.

It is certified that error appears in the above-identified patent and that said Letters Patent is hereby corrected as shown below:

In the Specification

In Column 3, Line 1, delete "the" and insert -- of the --, therefor.

In Column 5, Line 41, delete "(TOP), HA-TOP," and insert -- (TCP), HA-TCP, --, therefor.

In Column 7, Line 1, delete "A1" and insert -- A1. --, therefor.

In Column 9, Line 63, delete "incision 11" and insert -- incision I1 --, therefor.

In Column 9, Line 66, delete "incision 12" and insert -- incision I2 --, therefor.

In Column 12, Line 43, delete "incision 11 and/or incision 12" and insert -- incision I1 and/or incision I2 --, therefor.

In Column 15, Lines 1-2, delete "incision 11 and/or 12" and insert -- incision I1 and/or I2 --, therefor.

In Column 17, Line 48, delete "Range 268" and insert -- Flange 268 --, therefor.

In Column 18, Line 19, delete "incision 11 and/or incision 12" and insert -- incision I1 and/or incision I2 --, therefor.

Signed and Sealed this
Nineteenth Day of June, 2018

Andrei Iancu
*Director of the United States Patent and Trademark Office*